(12) United States Patent
Frantzen et al.

(10) Patent No.: US 8,728,800 B2
(45) Date of Patent: May 20, 2014

(54) ASSAY METHOD

(75) Inventors: Frank Frantzen, Olso (NO); Arne Ludvig Faaren, Olso (NO); Arne Kristian Nordhei, Olso (NO)

(73) Assignee: Axis Shield ASA, Oslo (NO)

( * ) Notice: Subject to any disclaimer, the term of this patent is extended or adjusted under 35 U.S.C. 154(b) by 815 days.

(21) Appl. No.: 11/664,540

(22) PCT Filed: Feb. 23, 2006

(86) PCT No.: PCT/GB2006/000638
§ 371 (c)(1),
(2), (4) Date: Feb. 6, 2008

(87) PCT Pub. No.: WO2006/090154
PCT Pub. Date: Aug. 31, 2006

(65) Prior Publication Data
US 2008/0261210 A1    Oct. 23, 2008

(30) Foreign Application Priority Data
Feb. 24, 2005 (GB) .................................. 0503836.9

(51) Int. Cl.
*G01N 33/53* (2006.01)
*G01N 33/533* (2006.01)
*C12Q 1/25* (2006.01)

(52) U.S. Cl.
USPC ................... 435/287.2; 435/283.1; 435/288.7

(58) Field of Classification Search
CPC combination set(s) only.
See application file for complete search history.

(56) References Cited

U.S. PATENT DOCUMENTS

| | | | | |
|---|---|---|---|---|
| 4,499,183 A | * | 2/1985 | Sujansky et al. .................. 435/6 |
| 5,173,418 A | * | 12/1992 | Molin et al. .................. 435/198 |
| 5,236,826 A | * | 8/1993 | Marshall ...................... 435/7.92 |
| 5,416,026 A | * | 5/1995 | Davis ............................... 436/66 |
| 5,428,729 A | * | 6/1995 | Chang et al. ................... 715/751 |
| 5,710,008 A | * | 1/1998 | Jackowski ...................... 435/7.4 |
| 6,064,474 A | * | 5/2000 | Lee et al. .......................... 356/39 |
| 6,096,563 A | | 8/2000 | Hajizadeh et al. |
| 6,649,419 B1 | | 11/2003 | Anderson |
| 2001/0039057 A1 | | 11/2001 | Douglas et al. |
| 2002/0125145 A1 | | 9/2002 | Ohara et al. |
| 2004/0161368 A1 | | 8/2004 | Holtlund et al. |
| 2006/0019319 A1 | * | 1/2006 | Billadeau et al. ............ 435/7.21 |

FOREIGN PATENT DOCUMENTS

| | | | |
|---|---|---|---|
| EP | 1 176 424 A2 | 1/2002 | |
| JP | 59-168371 A | 9/1984 | |
| JP | 2002-107365 A | 4/2002 | |
| WO | WO93/15220 | * 8/1993 | ............... C12Q 1/34 |
| WO | WO00/40973 | * 7/2000 | ............ G01N 33/68 |
| WO | WO 02/090995 A3 | 11/2002 | |

OTHER PUBLICATIONS

Frantzen et al., "Enzyme conversion immunoassay for determining total homocysteine in plasma or serum," Clinical Chemistry, Feb. 1998, vol. 44, pp. 311-316.*
Frick et al., "Rapid measurement of total plasma homocysteine by HPLC," Clinica Chimica ACTA, May 2003, vol. 331, pp. 19-23.*
Kucia et al., Circ Res. 2004; 95:1191-1199.*
O'Broin et al., (Am J Clin Nutr 1999; 70:359-67).*
F. Frantzen, et al. "Enzyme conversion immunoassay for determining total homocysteine in plasma or serum", Clinical Chemistry, American Association for Clinical Chemistry, Washington, DC, Feb. 1998, vol. 44, No. 2, pp. 311-316.
Barbara Frick et al., "Rapid measurement of total plasma homocysteine by HPLC", Clinica Chimica ACTA; International Journal of Clinical Chemistry, May 2003, vol. 331, No. 1-2, pp. 19-23.
"Notification of Reasons for Rejection" issued by the Japanese Patent Office on Oct. 19, 2010, in corresponding Japanese Patent Application No. 2007-556660, 3 pages. (English Translation Attached, pp. 1-4.)

* cited by examiner

*Primary Examiner* — Jacob Cheu
*Assistant Examiner* — Carmencita M Belei
(74) *Attorney, Agent, or Firm* — Bacon & Thomas, PLLC

(57) ABSTRACT

The invention provides a cassette-based automated assay for homocysteine.

13 Claims, 26 Drawing Sheets

ASSAY METHOD

RELATED APPLICATIONS

The present application is a National Stage under 371 of International Application No. PCT/GB06/00638, filed on Feb. 23, 2006, which claims priority to Great Britain Application No. 0503836.9, filed on Feb. 24, 2005, the entire contents of which are incorporated herein by reference.

FIELD

The present invention relates to a method of assaying for homocysteine in blood and to assay kits for use in such a method.

BACKGROUND

Homocysteine (HCy) is a small sulphur-containing alpha amino acid not used in protein synthesis but present in cells and extracellular fluid in low concentrations, e.g. typically about 10 µM in adult human blood plasma. Elevated plasma HCy levels have been associated with folate or vitamin B deficiency and with cardiovascular disease. There is thus significant clinical interest in assaying for HCy in plasma.

One such assay system was developed by Axis-Shield ASA and is available commercially from Abbott Laboratories. In the first six years of sales, over 26 million such HCy assays have been carried out using this system. The Axis-Shield/Abbott HCy assay involves enzymatic conversion of HCy in plasma to S-adenosyl-homocysteine (SAH) and immunoassay detection of the SAH. The Axis-Shield/Abbott HCy assay however is designed to be carried out in clinical laboratories and there remains a need for an HCy assay which is in a format performable at the point-of-care, e.g. in the physician's office, so that the patient need not revisit to learn the outcome of the assay.

An assay performing device capable of use at the point-of-care has recently been developed by Axis-Shield ASA. This is available commercially under the trade mark Afinion and is described for example in WO 02/090995, the contents of which are hereby incorporated by reference. In the Afinion system, a sample (e.g. blood, plasma, urine, etc) is placed in an assay cartridge which contains several wells pre-loaded with the reagents required for the performance of the assay and carries computer-readable information sufficient to enable the device to determine how to perform the assay for the particular sample type and analyte of interest.

SUMMARY

We have now developed an assay for plasma HCy capable of being carried out at the point-of-care, e.g. using an Afinion device, using whole blood, i.e. without requiring separation of cells from the blood sample.

The ability to use whole blood rather than plasma greatly simplifies the sample handling required of the physician.

The use of whole blood however raises serious problems for the performance of a plasma HCy assay as intracellular HCy in the sample may potentially leak into the plasma. Indeed, for the current clinical laboratory assay for plasma HCy, the physician is instructed to separate plasma from whole blood and store the plasma sample cold within 30 minutes so as to avoid contamination by intracellular HCy. Contamination by intracellular HCy has to be avoided as the current standards for normal/abnormal blood HCy are for plasma HCy and it is not known how much patient-to-patient variability there is in intracellular HCy and how much this varies according to patient health.

We have now found however that it is possible to use unseparated whole blood samples in an enzymatic immunoassay for plasma HCy by delaying cell lysis until binding has taken place and by correcting for hematocrit.

DETAILED DESCRIPTION

Thus viewed from one aspect the invention provides a method of assaying for plasma homocysteine in a blood sample taken from a human or vascularized non-human animal subject, said method comprising: contacting a whole blood sample from said subject with the following reagents—a liquid diluent, a reducing agent, a homocysteine-converting enzyme, optionally an inhibitor of the homocysteine converting reaction of said enzyme, a cell-lysing agent, a color-labelled binding agent capable of binding to a conversion product of said homocysteine-converting enzyme, and a particulate capable of competing with said conversion product for binding to said binding agent; following contact with said reagents, drawing said sample through a membrane having a porosity sufficient to allow passage therethrough of said binding agent in its unbound state and when bound to said conversion product but insufficient to allow passage therethrough of said binding agent when bound to said particulate; detecting the color-label of said binding agent retained on said membrane; determining therefrom an indication of the plasma homocysteine concentration by applying a correction factor dependent on red blood cell concentration in said whole blood sample; and optionally but preferably presenting the plasma homocysteine concentration as a visible or electronic signal; wherein contact with said reagents is sequential or simultaneous subject to the provisos that:
i) contact with said lysing agent occurs after contact with said diluent, enzyme and reducing agent;
ii) contact with the inhibitor, where present, occurs after contact with said diluent, enzyme and reducing agent and no later than contact with said lysing agent; and
iii) contact with said binding agent and said particulate does not involve contact with a liquid containing both said binding agent and said particulate.

In the method of the invention, it is preferred to take steps to terminate or at least decelerate the conversion of HCy by the homocysteine converting enzyme before (or at the same time as) cell lysis is begun. This may be achieved by changing the sample temperature, e.g. to slow down the enzymatic reaction or to denature the enzyme, or by dilution, or by altering the pH, or by adding an agent which serves to inhibit the reaction or to denature the enzyme (e.g. using a detergent such as SDS, a chaotropic salt such as NaSCN, or another known denaturing agent such as urea or guanidinium chloride, or a metal or co-factor binding agent (where the enzymatic reaction requires a metal or a cofactor)). Where a denaturing detergent is used, this could also function as the lysing agent. For convenience sake, such agents which interfere with the enzymatic HCy conversion reaction are referred herein as inhibitors and in a preferred embodiment of the method of the invention an inhibitor is included in the set of reagents used.

In the method of the invention, contact with the reagents preferably involves incubation for a predetermined time and preferably at a predetermined temperature in two stages, firstly when contact with diluent, reducing agent and enzyme has been made, and secondly and subsequently when contact with particulate and binding agent has been made.

In a first preferred embodiment the contact sequence is as follows:

i) contact with diluent,
ii) contact with enzyme and reducing agent, iii) incubate,
iv) contact with particulate, inhibitor and lysing agent,
v) contact with binding agent,
vi) incubate, and
vii) draw through membrane.

In a second, more preferred embodiment the contact sequence is as follows:
i) contact with diluent,
ii) contact with reducing agent, enzyme and particulate,
iii) incubate,
iv) contact with lysing agent, inhibitor and binding agent,
v) incubate, and
vi) draw through membrane.

In a third preferred embodiment the contact sequence is as follows:
i) contact with diluent,
ii) contact with reducing agent, enzyme and particulate,
iii) incubate,
iv) contact with lysing agent and inhibitor,
v) contact with binding agent,
vi) incubate, and
vii) draw through membrane.

In general it is preferred that the reagents be presented in a single-use, multi-walled assay cartridge. Particularly preferably such a cartridge should contain the reagents, a pipette tipped with the membrane, and a removable capillary-tipped pipette. In such a cartridge it is especially preferred that at least the binding agent and the enzyme and preferably also the particulate be presented in dry form with the binding agent and particulate being present in separate wells.

Thus viewed from a further aspect the invention provides a single-use cartridge for a plasma homocysteine assay using whole blood, said cartridge having a multi-welled base, a removable capillary-tipped pipette, and a cover, said cover carrying a membrane-tipped pipette, and the wells of said base containing the following assay reagents: a liquid diluent; a reducing agent; a homocysteine-converting enzyme; optionally, an inhibitor of the homocysteine converting reaction of said enzyme; a cell-lysing agent; a color-labelled binding agent capable of binding to a conversion product of said enzyme; and a particulate capable of competing with said conversion product for binding to said binding agent; said binding agent and said particulate being in different said wells; where present, said inhibitor and said enzyme being in different said wells; and said lysing agent being in a well different from the well or wells containing said enzyme and at least part of said reducing agent and said diluent.

In a first preferred embodiment, the cartridge comprises at least four wells, a first containing diluent, a second containing enzyme and reducing agent, a third containing particulate, lysing agent and inhibitor, and a fourth containing binding agent. In a second preferred embodiment, the cartridge comprises at least four wells, a first containing diluent, a second containing diluent, inhibitor and lysing agent, a third containing enzyme, reducing agent and particulate, and a fourth containing binding agent. In a third preferred embodiment, the cartridge comprises at least four wells, a first containing diluent, a second containing enzyme, reducing agent and particulate, a third containing diluent, inhibitor and lysing agent, and a fourth containing binding agent. These three cartridge formats are especially suited for performance of the preferred contact sequences listed above.

The wells of the cartridges of the invention, where they contain a liquid, are preferably provided with removable or perforatable closures, e.g. foil seals. The cover preferably comprises a piercer for piercing such seals and preferably is shaped to hold the removable pipette which itself can be used to take up a whole blood sample for introduction into the cartridge.

Before use, the cartridge is preferably disposed in a sealed container, e.g. a foil pack, which preferably also contains a drying agent, e.g. silica gel or a molecular sieve.

Thus assay performance using the first preferred cartridge embodiment suitably involves the following steps:
1) Dip the capillary in blood and place the capillary-tipped pipette in the cartridge;
2) Place the cartridge in the assay device and initiate automated assay performance (i.e. the steps listed below are performed automatically);
3) Remove cover from base and unseal any sealed wells;
4) Introduce diluent into the capillary-tipped pipette from the first well;
5) Introduce blood and diluent from the capillary-tipped pipette into the second well;
6) Allow the contents of the second well to incubate for a preset period;
7) During incubation, introduce diluent from the first well into the third well using the capillary-tipped pipette;
8) Introduce incubated liquid from the second well into the third well using the capillary-tipped pipette;
9) Introduce binding agent and diluent from the fourth well into the third well using the capillary-tipped pipette;
10) Allow the contents of the third well to incubate for a preset period;
11) Introduce incubated liquid from the third well into the membrane-tipped pipette by passage through the membrane;
12) Detect binding agent retained on the outer surface of the membrane; and
13) Determine plasma HCy content and display and/or export the result.

An assay performance sequence for the second preferred cartridge embodiment is as follows:
1) Dip the capillary in blood and place the capillary-tipped pipette in the cartridge;
2) Place the cartridge in the assay device and initiate automated assay performance (i.e. the steps listed below are performed automatically);
3) Remove cover from base and unseal any sealed wells;
4) Introduce diluent into the capillary-tipped pipette from the first well;
5) Introduce blood and diluent from the capillary-tipped pipette into the third well;
6) Allow the contents of the third well to incubate for a preset period;
7) During incubation, introduce diluent from the first well and/or the second well into the fourth well using the capillary-tipped pipette;
8) Introduce diluent, lysing agent and inhibitor from the second well into the third well using the capillary-tipped pipette;
9) Introduce binding agent and diluent from the fourth well into the third well using the capillary-tipped pipette;
10) Allow the contents of the third well to incubate for a preset period;
11) Introduce incubated liquid from the third well into the membrane-tipped pipette by passage through the membrane;
12) Detect binding agent retained on the outer surface of the membrane; and
13) Determine plasma HCy content and display and/or export the result.

An assay performance sequence for the third preferred cartridge embodiment is as follows:
1) Dip the capillary in blood and place the capillary-tipped pipette in the cartridge;

2) Place the cartridge in the assay device and initiate automated assay performance (i.e. the steps listed below are performed automatically);
3) Remove cover from base and unseal any sealed wells;
4) Introduce diluent into the capillary-tipped pipette from the first well;
5) Introduce blood and diluent from the capillary-tipped pipette into the second well;
6) Allow the contents of the second well to incubate for a preset period;
7) During incubation introduce diluent from the third well into the fourth well using the capillary-tipped pipette;
8) Introduce incubated liquid from the second well into the third well using the capillary-tipped pipette;
9) Introduce binding agent and diluent from the fourth well into the third well using the capillary-tipped pipette;
10) Allow the contents of the third well to incubate for a preset period;
11) Introduce incubated liquid from the third well into the membrane-tipped pipette by passage through the membrane;
12) Detect binding agent retained on the outer surface of the membrane; and
13) Determine plasma HCy content and display and/or export the result.

One or more of the reagents used in the assay method of the invention may be presented in solid or semi-solid form, e.g. as films, powders or beads. The use of reagents in bead form is particularly advantageous when the assay is performed using a reagent-loaded cartridge as described herein as it increases the flexibility of cartridge loading and assay performance design, not least because reagents which might interact during cartridge storage may be presented in bead form in the same cartridge wells without interaction problems during storage occurring. Moreover the storage stability of individual reagents may be greater in bead form than in solution form.

As a result, in three further preferred embodiments of the invention, the assay cartridge contains selected reagents in bead form. Thus, in a fourth preferred embodiment, the cartridge comprises at least five wells: a first containing diluent and cell-lysing agent; a second containing diluent; a third containing a first bead containing binding agent and a second bead containing particulate; a fourth containing a third bead containing inhibitor; and a fifth containing a fourth bead containing enzyme and reducing agent, and optionally, but preferably, a fifth bead containing nuclease.

In the fifth preferred embodiment, the cartridge comprises at least five wells: a first containing diluent and cell-lysing agent; a second containing diluent and optionally but preferably nuclease; a third containing a first bead containing binding agent and a second bead containing particulate; a fourth containing a third bead containing inhibitor; and a fifth containing a fourth bead containing enzyme and reducing agent. In the sixth preferred embodiment, the cartridge comprises at least five wells: a first containing diluent and cell-lysing agent; a second containing diluent and optionally but preferably nuclease; a third containing a first bead containing binding agent and a second bead containing particulate; a fourth free of reagents; and a fifth containing inhibitor and, separately, a third bead containing enzyme and reducing agent.

In these embodiments, any beads in the fifth and fourth wells are desirably inside the capillary-tipped or membrane-tipped pipettes respectively. Where the fifth well contains beads, this is preferably in the reservoir of the capillary-tipped pipette. In the embodiments just described these beads contain enzyme and reducing agent. In the sixth embodiment the fifth well also contains inhibitor, e.g. in dried form in an inverse conical plastic cup at the base of the well, i.e. separate from the beads.

Thus assay performance using the fourth and fifth preferred cartridge embodiments suitably involves the following steps:
1) Dip the capillary in blood and place the capillary-tipped pipette in the cartridge;
2) Place the cartridge in the assay device and initiate automated assay performance (i.e. the steps listed below are performed automatically);
3) Remove cover from base and unseal any sealed wells;
4) Introduce diluent into the capillary-tipped pipette from the second well;
5) Flush blood, diluent and enzyme from the capillary-tipped pipette into the second well;
6) Allow the contents of the second well to incubate;
7) Introduce diluent and cell-lysing agent from the first well into the membrane-tipped pipette and flush back into the first well;
8) Using the capillary-tipped pipette, introduce diluent, cell-lysing agent and inhibitor from the first well into the second well;
9) Using the capillary-tipped pipette, introduce lysed sample from the second cell into the third well;
10) Allow the contents of the third well to incubate;
11) Introduce incubated liquid from the third well into the membrane-tipped pipette by passage through the membrane;
12) Detect binding agent retained on the outer surface of the membrane; and
13) Determine plasma HCy content and display and/or export the result.

Assay performance using the sixth preferred cartridge embodiment suitably involves the following steps:
1) Dip the capillary in blood and place the capillary-tipped pipette in the cartridge;
2) Place the cartridge in the assay device and initiate automated assay performance (i.e. the steps listed below are performed automatically);
3) Remove cover from base and unseal any sealed wells;
4) Introduce diluent into the capillary-tipped pipette from the second well;
5) Flush blood, diluent and enzyme from the capillary-tipped pipette into the second well;
6) Allow the contents of the second well to incubate;
7) Using the capillary-tipped pipette introduce diluent and cell lysing agent from the first well into the fifth well to dissolve the inhibitor;
8) Using the capillary-tipped pipette transfer diluent, cell-lysing agent and inhibitor from the fifth well into the first well;
9) Using the capillary-tipped pipette transfer diluent, cell-lysing agent and inhibitor from the first well into the second well;
10) Using the capillary-tipped pipette, introduce lysed sample from the second cell into the third well;
11) Allow the contents of the third well to incubate;
12) Introduce incubated liquid from the third well into the membrane-tipped pipette by passage through the membrane;
13) Detect binding agent retained on the outer surface of the membrane; and
14) Determine plasma HCy content and display and/or export the result.

In each case, the hemoglobin content of the sample is preferably determined spectrophotometrically before uptake of the sample through the membrane. Desirably this is done after the sample has been contacted with the cell-lysing agent.

Where liquid is transferred from one well to another, this will generally not be the entire liquid contents of the donor well but instead a predetermined volume.

The homocysteine-converting enzyme used in the method of the invention may be any one which produces a homocysteine conversion product which is capable, directly or indirectly, of binding to the binding agent. Indirect binding in this regard means that the initial enzymatic conversion product may be used as a reactant in a further reaction a product of which can bind to the binding agent. Several homocysteine converting enzymes are known and may be used, e.g. cystathionine beta synthase, homocysteinase, homocysteine desulphurase, methionine synthase, dimethyl thetin homocysteine methyl transferase, betaine-homocysteine methyl transferase, 5-methyltetrahydrofolate-homocysteine S-methyl transferase, 5-methyltetrahydropteroyltriglutamate-homocysteine S-methyl transferase, O-succinylhomoserine-beta-lyase, and S-adenosyl homocysteine hydrolase (SAH-hydrolase).

The use of SAH-hydrolase, in particular recombinant SAH-hydrolase, is preferred. The enzymatic conversions of homocysteine using these enzymes may require a further reactant, a "co-substrate", such as adenosine or an adenosine analog in the case of SAH-hydrolase, or water in the case of homocysteinease. Where a co-substrate is required, this should generally be provided as a reagent in the assay method and cartridge of the invention. Such a co-substrate should be contacted with the blood sample in time for the first incubation and may typically be present in the diluent or with the enzyme.

Where the enzyme is SAH-hydrolase, the analyte will generally be adenosine or SAH or an enzymatic conversion product of one of these. SAH however is the preferred analyte. Where the enzyme is homocysteine desulphurase, the analyte will generally be an enzymatic conversion product of alpha-keto butyrate.

The diluent used according to the invention is preferably aqueous, e.g. water or an aqueous buffer, e.g. phosphate, carbonate, borate, MOBS, HEPES, Tris or glycylglycine buffer, typically having a pH of 6 to 10, more preferably 7 to 9, especially 7.2 to 8.5. Other buffers having such pHs may of course be used.

The reducing agent used according to the present invention serves to convert the various forms in which HCy may occur in plasma into free homocysteine. This use of a reducing agent is conventional in plasma HCy assays. Examples of suitable reducing agents that may be used include dithiols (particularly dithiothreitol (DTT), dithioerythrol (DTE) and bis-(2-mercaptoethyl)sulphone), phosphines (e.g. tris(2-carboxyethyl)phosphine (TCEP), triphenylphosphine and tri-n-butyl-phosphine), boranes (e.g. borane-tetrahydrofuran complex, dimethylsulphide-borane, and decaborane), borohydrides (e.g. $NaCNBH_3$, $NaBH_4$ and triacetoxyborohydride), hydrides (e.g. $LiAlH_4$) and silanes (e.g. alkylsilanes such as $Et_3SiH$, phenylsilanes and tris(trimethylsilyl)silane). The use of tris-(2-carboxyethyl)phosphine:HCl (TCEP) is especially preferred.

The inhibitor used according to the invention serves to terminate the homocysteine conversion before the cells in the sample are lysed so as to prevent the plasma HCy value determined by the assay from being contaminated by any significant contribution from the intracellular HCy. Enzyme inhibitors are well known. Such inhibitors generally combine directly with the enzyme to inhibit its performance, e.g. by mimicking the properties of the natural substrate, thereby for example leading to blocking of the enzyme or production of another product. Others however can act on a substrate or cofactor or on molecules or intermediates formed during the enzymatic process (thereby preventing formation of the normal end product). In the case of SAH-hydrolase for example, reagents which react with or interfere with thiol groups will function as inhibitors since a free thiol group is required for biological action of this enzyme. Examples include merthiolate and maleimido compounds (e.g. N-ethylmaleimide). Examples of other inhibitors include adenine analogs and adenine nucleosides. Further inhibitors include: D-eritadenine, 9-D-xylofuranosyladenine, adenine 9-β-D-arabinofuranoside, erythro-9-(2-hydroxy-3-nonyl)-adenine, periodo-oxidized adenosine, 2'-deoxyadenosine, 3'-deoxyadenosine, 2',3'-dideoxyadenosine, carbocyclic adenosine, 2-chloro-adenosine, 2-chlorodeoxyadenosine, adenosine dialdehyde, N6-methyladenosine, coformycin, 2'-deoxycoformycin, formycin, 2-amino-6-chloro-purine riboside, nebularin, pyrazomycin, 3-deaza (+/−)-aristeromycin, aristeromycin (and its halovinyl derivatives), tubericin, and ara-A and derivatives thereof (e.g. 2-chloro-ara-A). The use of merthiolate is preferred; however the use of N-ethylmaleimide is especially preferred, e.g. at a working concentration of 300 μg/mL. Links to publications concerning recombinant SAH-hydrolase and various materials which inhibit its functioning may be found at http://www.pdg.cn-b.uam.es/UniPub/iHOP/gs/95822.html.

The cell lysing agent used according to the invention serves to break down the blood cells so that they are not retained on the outer surface of the membrane. Cell lysing agents are well known and suitable cell lysing agents for use according to the invention include detergents, e.g. urea, deoxycholate, empigen, ammonyx, SDS, thesit (e.g. Lubrol PX and C12E9), and Triton X100 (e.g. Nonidet P40). The use of SDS at a working concentration of 0.4% wt. is preferred.

In an assay method, such as that of the present invention, in which cells in a sample are lysed before the sample is drawn through a porous membrane and material retained by the membrane is detected, DNA released by cell lysis can at least partially clog the pores of the membrane. This is particularly the case where the sample contains a high concentration of white blood cells. Membrane pore clogging may thus be reduced by the use of a DNAse, i.e. a nuclease, to digest the DNA released by cell lysis. The nuclease may be contacted with the sample at any time before the sample is drawn through the membrane.

The nuclease may require an activator, e.g. a group 2 metal ion such as $Mg^{2+}$, and in this event contact with the activator may occur before, during or after contact with the nuclease as long as it also occurs before the sample is drawn through the membrane. Preferably however contact with the activator occurs at the same time as contact with the nuclease. Nucleases and the activators they require are well known and are commercially available, e.g. as Benzonase from Merck.

The binding agent used according to the invention may be any material which binds preferentially to the enzyme conversion product and its competitor (the particulate) relative to the other materials present in the sample. It consists of two functional parts covalently or otherwise bound or held together, namely a color label and a binding moiety. The color-label is desirably a material which absorbs, emits, scatters or generates light in the visible range, e.g. a chromophore or fluorophore. However color-labels which absorb, emit, scatter or generate light in the infrared or UV range may be used. Thus, the color label may be any spectrophotometrically detectable moiety, such as for example a chromophore or fluorophore, or an enzyme label (e.g. alkaline phosphatase, horseradish peroxidase, or firefly luciferase) that can generate a colour, fluorescent, light emitting or scattering signal that can be spectrophotometrically read. Particularly preferably clustered colloidal gold or other metal, e.g. having a mode particle size for the clusters of about 100 to 200 nm is used.

The binding moiety may be an antibody or fragment or construct thereof or a small organic molecule, etc. The use of antibodies and antibody fragments or constructs is preferred. Where the enzyme used is SAH-hydrolase, it is preferred to use anti-SAH antibodies, particularly recombinant such antibodies. Antibodies of this type are described for example in the patent publications of Axis-Shield ASA, for example WO 00/40973 the disclosures of which are incorporated herein by reference. More specifically, monoclonal anti-SAH antibodies may be produced as described in Example 1 of WO 00/40973. Coupling of colloidal gold to such antibodies may be effected as described in U.S. Pat. No. 5,691,207 and U.S. Pat. No. 5,650,333.

The particulate used according to the invention may be any material which may be suspended in the diluent and retained by the membrane. Again it has two functional components—a bulky entity causing membrane retention and a competitor for binding to the binding agent, with the two being coupled by covalent bonding or other interaction. The bulky agent is preferably white or colourless, e.g. polymer particles, for example latex particles. The competitor moiety will typically be the enzyme conversion product or an analog or fragment thereof. Where the enzyme is SAH-hydrolase, the competitor is preferably S-adenosyl-cysteine. The chemical technique used to couple the competitor to the bulky moiety clearly depends on the nature of the functional groups available for reaction on the latter. Typically linking agents such as water-soluble cardodiimides, such as 1-ethyl-3-(dimethylamino-propyl)-carbodiimide, EDC/EDAC, homobifunctional linking agents such as bis(sulpho-succinimidyl)suberate, $BS_3$, may be used or coupling may be effected directly if the bulky moiety carries reactive or preactivated groups such as chloromethyl or aldehydes. Preferably, the competitor is first coupled to a protein (e.g. albumin or more preferably thyroglobuline) before the protein-competitor conjugate is coupled to the bulky moiety. Such coupling chemistry is well established in the art.

The membrane used according to the invention may be any material with a porosity such as to retain the particulate but allow transmission of the binding agent and its conjugates with the conversion product. The factors that should be taken into account when selecting the membrane material include pore-size, strength and attachability. The pore-size should be sufficiently small to stop the desired conjugates yet sufficiently large to allow transmission of non-conjugated materials and the undesired conjugates. The use of small particulates (e.g. 0.1 to 1.0 µm) gives a better signal than large particulates (e.g. 1 to 10 µm) but also leads to greater membrane clogging. Accordingly the preferred particulate size is 1 to 2 µm and the membrane pore size is preferably chosen accordingly. The use of hydrophilic polyethersulphone and acrylcopolymer membranes, e.g. with pore sizes above 0.8 µm is preferred. Such membranes are available as Supor and Versapor from Pall. The membrane may be adhered or welded to its pipette; preferably it is planar, disposed at a slant to the axis of the pipette (i.e. between perpendicular and parallel).

This arrangement is described in WO 02/090995 and appears in the Afinion cartridges sold by Axis-Shield ASA.

Desirably, at least the pipette-free wells in the cartridges used according to the invention are rectangular in cross-section with flat, transparent bases which are slanted at an angle to the plane perpendicular to the well axis.

In order for the enzyme reaction(s) to take place sufficiently completely for adequate analyte to be produced, it is, as mentioned above, desirable to incubate the sample. Likewise in order for sufficient binding agent conjugation to take place for an adequate signal to be produced, it is desirable to carry out a second incubation of the sample. In other words neither reaction needs to go to equilibrium and the incubation times should desirably be kept as short as is compatible with the desired accuracy of the assay so as to optimize assay acceptability to the user. Typically such incubations will be at 20 to 45° C., preferably 30 to 45° C. and most preferably 36 to 42° C. Suitable incubation times will generally be in the range 0.5 to 10 minutes, preferably 0.75 to 5 minutes, more preferably 1 to 3 minutes. For the enzymatic incubation, the most preferred range is 1 to 2 minutes.

In order that the determined value for plasma HCy may be corrected for the relative plasma content of the blood sample (since hematocrit can vary from patient to patient), either the physician must input a value for (or indicative of) hematocrit or, and more preferably, a value for (or indicative of) hematocrit must be determined in the course of the assay.

To this end the hemoglobin content of the sample may be measured spectrophotometrically either before, or more preferably after, cell lysis. Where measurement is made before cell lysis, a background correction will preferably be made, e.g. using a spectrophotometric measurement made in the infra-red range. Where the determined hematocrit value is abnormally low, e.g. below 0.3, more especially below 0.25, the method of the invention will preferably also present (visually or electronically) either the hematocrit value or a warning that it is low. If desired the hematocrit value may in any event be presented.

Determination of hemoglobin content may be by light scattering, transmission or reflectance. Preferably it will be absorption, for example using green or blue diodes as the light source. Determination of binding agent concentration remaining on the membrane will generally be by reflectance, e.g. using green or blue diodes as the light source.

As with most assays, it is preferred that the assay is calibrated, e.g. using standards with known HCy content. The calibration data for the reagents used will preferably be provided with the cartridges, e.g. encoded in bar or other machine readable codes on the cartridge or its packaging.

The method of the invention is particularly effective at quantifying plasma HCy levels of up to 30 µM. Where plasma HCy is above 30 µM the assay output may simply indicate that the plasma HCy content is abnormally high. Normal levels are generally 10-15 µM or lower and physician intervention is called for at higher levels, e.g. vitamin B or folate supplementation or investigation for cardiovascular problems, etc. Lower than normal plasma HCy values are not generally seen to be problematic and in infants and patients taking multivitamin supplements values may be as low as about 5 µM.

The performance of diagnostic assays on whole blood in order to determine the plasma content of an extracellular analyte which also occurs in blood cells is novel and forms a further aspect of the invention. Viewed from this aspect the invention provides a method of assaying for an analyte present in plasma and in blood cells, said method comprising (a) determining the content of said analyte in plasma of a whole blood sample, (b) determining (preferably spectrophotometrically) the hematocrit or hemoglobin content of said sample, and (c) determining therefrom the plasma concentration of said analyte.

Thus step (a) may involve reacting the analyte in the plasma of a whole blood sample to produce a detectable species while the cells in said sample are intact, lysing said cells under conditions in which intracellular analyte will not react to form said product and detecting said product.

Where reagents are presented in bead form, these may be water-insoluble beads coated or impregnated with dried reagent and optionally an inert and preferably non-hygroscopic binder (e.g. a sugar such as trehalose, or PEG); however the beads are preferably water-soluble comprising reagent and an inert binder. Such beads may be prepared for example by freezing 5 to 100 µL (preferably 10-50 µL) droplets of a buffered reagent solution and then freeze drying the frozen droplets.

The use of such reagent beads in diagnostic assays, in particular cartridge-based assays, is novel and forms a further aspect of the invention. Thus viewed from a further aspect the invention provides a single-use cartridge for a diagnostic assay, e.g. an assay for an analyte in a body fluid, mass or tissue sample, comprising a cartridge body having a plurality of wells at least one of which, preferably at least 2 of which, contain reagents for the performance of said assay, characterized in that at least one well contains a bead which in a solvent (e.g. water) releases at least one said reagent. The reagents presentable in bead form include for example analyte binding agents, competitive binding particulates, enzymes (e.g. nucleases, analyte (e.g. homocysteine)-converting enzymes, etc.), etc. While the analyte assayed for using such cartridges is preferably homocysteine it may be any other appropriate analyte, e.g. C-reactive protein, clotting factors, transferrin, ferritin etc.

The method and cartridges of the invention will now be described further with reference to the following non-limiting Examples and the accompanying drawings.

BRIEF DESCRIPTION OF THE DRAWINGS

FIG. 8 comprises schematic drawings showing the relative positions of cartridge components in the stages shown in FIG. 1.

In FIG. 8B, 5 to 10 µL of a blood sample (13) is shown in the capillary pipette of well A;

In FIG. 5T, the sample in the capillary pipette is emptied into Well C;

Referring to FIG. 1, there is shown a five well assay cartridge comprising a clear plastic base 1 having therein five wells 2, 3, 4, 5, 6 (referred to in the Examples as Wells E, D, C, B and A respectively) and a support leg 7. Wells, 2, 3 and 4 are sealed with foil 8. Cartridge cover 9 (only partly shown) comprises a removable capillary tipped pipette 10 and a fixed pipette 11 having a membrane tip 12. The contents of Wells 2 to 4 are as described in Example 1.

The arrows shown represent the sequential material transfers set out in Example 2.

Figure 1:
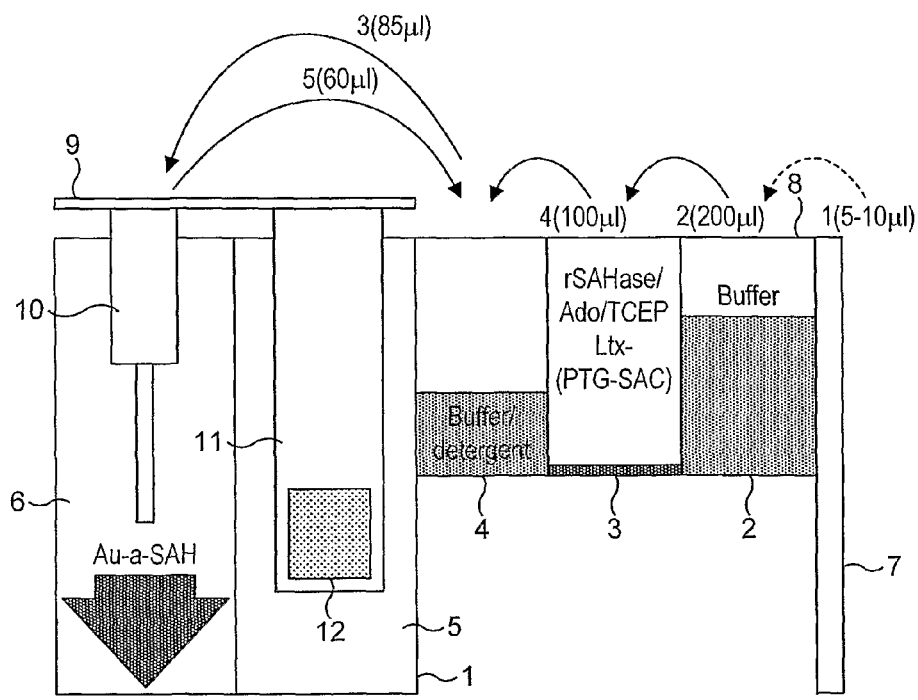
FIGS. 1 to 7 are schematic drawings of cartridges according to the invention showing material transfer stages in the performance of an assay method according to the invention.
Figure 2:
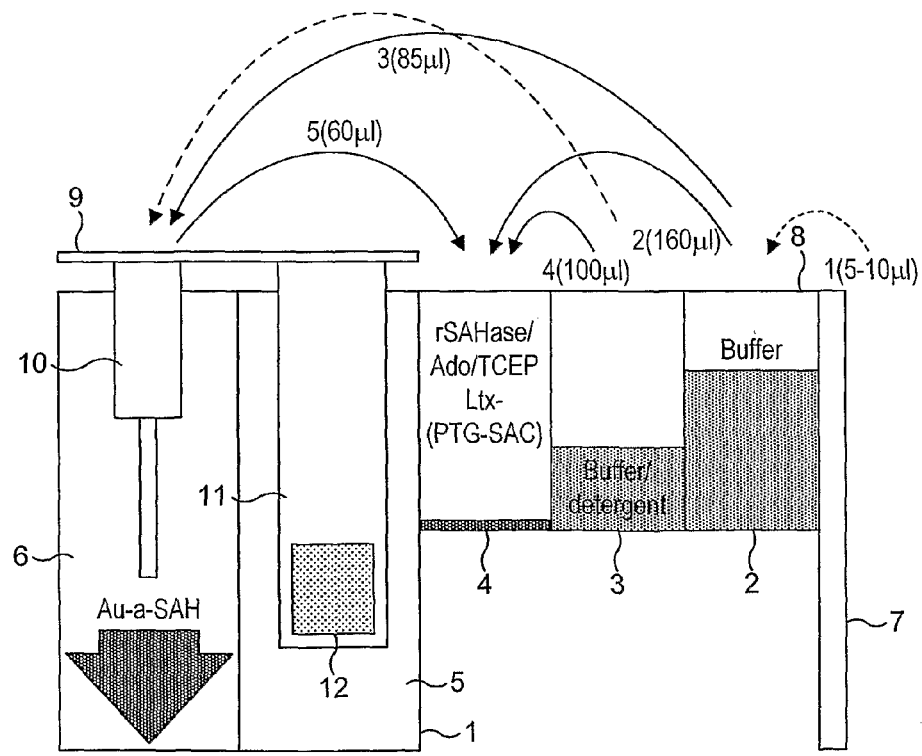

FIG. 2 is analogous to FIG. 1 except that the contents of Wells 2 to 4 are as described in Example 3 and the arrows represent the sequential material transfer set out in Example 4.

Figure 3:
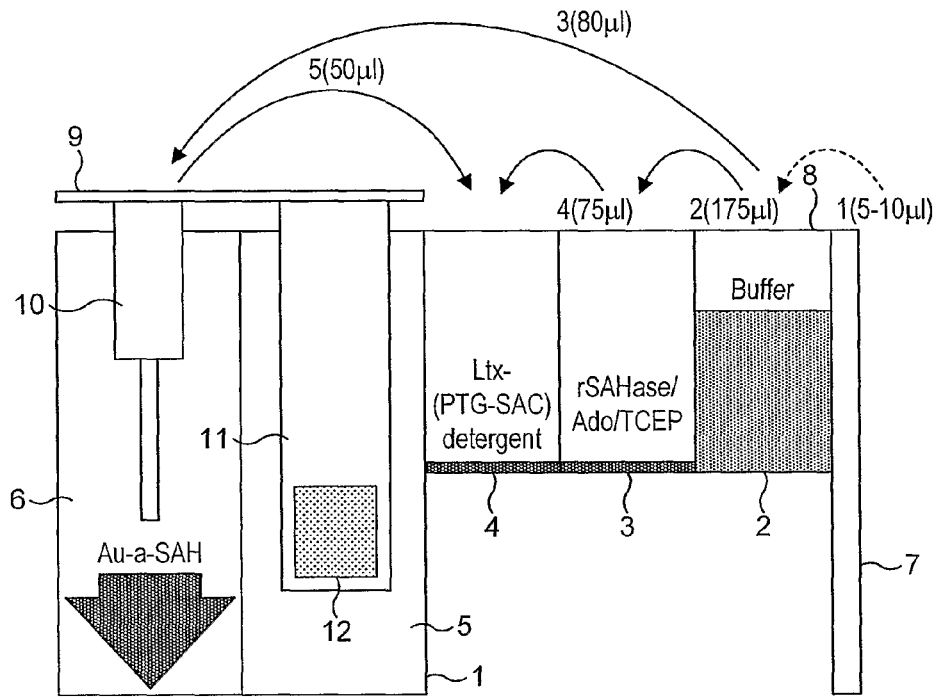

FIG. 3 is analogous to FIG. 1 except that the contents of Wells 2 to 4 are as described in Example 5 and the arrows represent the sequential material transfer set out in Example 6.

Figure 4:
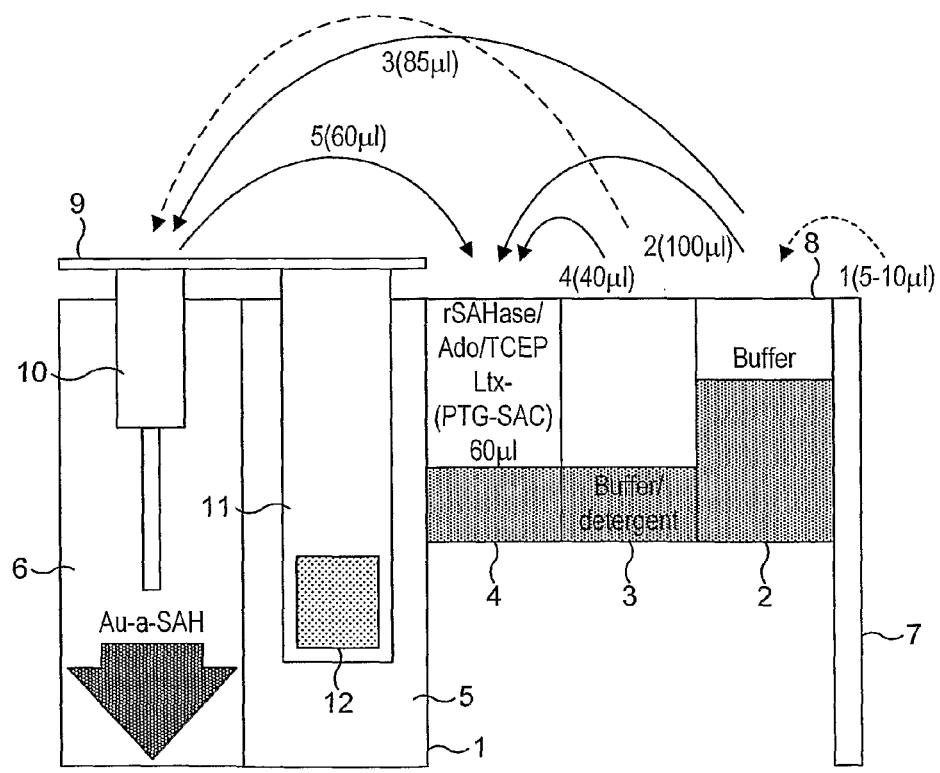

FIG. 4 is analogous to FIG. 1 except that the contents of Wells 2 to 4 are as described in Example 7 and the arrows represent the sequential material transfer set out in Example 8.

Figure 5:
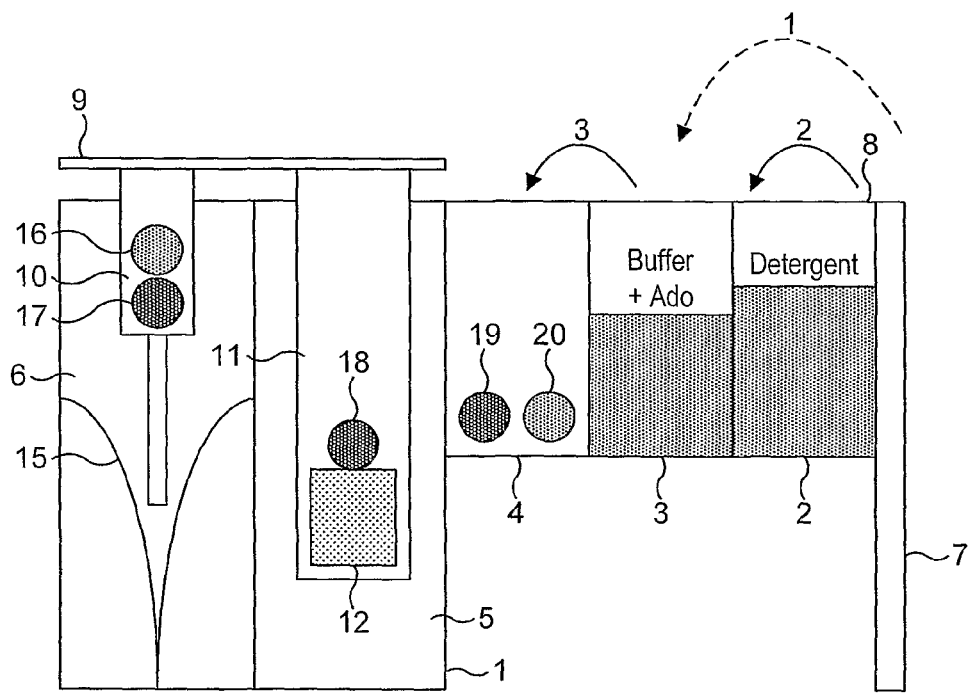

FIG. 5 is analogous to FIG. 1 except that the contents of Wells 1 to 5 are as described in Example 9 and the arrows represent the sequential material transfer set out in Example 10.

Figure 6:
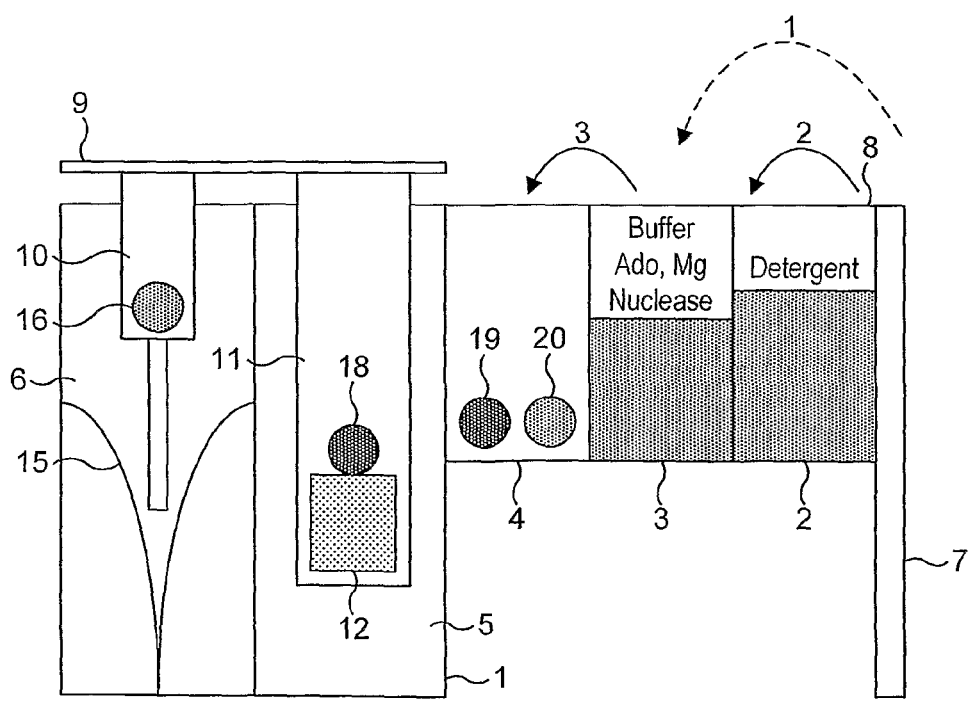

FIG. 6 is analogous to FIG. 1 except that the contents of Wells 1 to 5 are as described in Example 11 and the arrows represent the sequential material transfer set out in Example 12.

Figure 7:
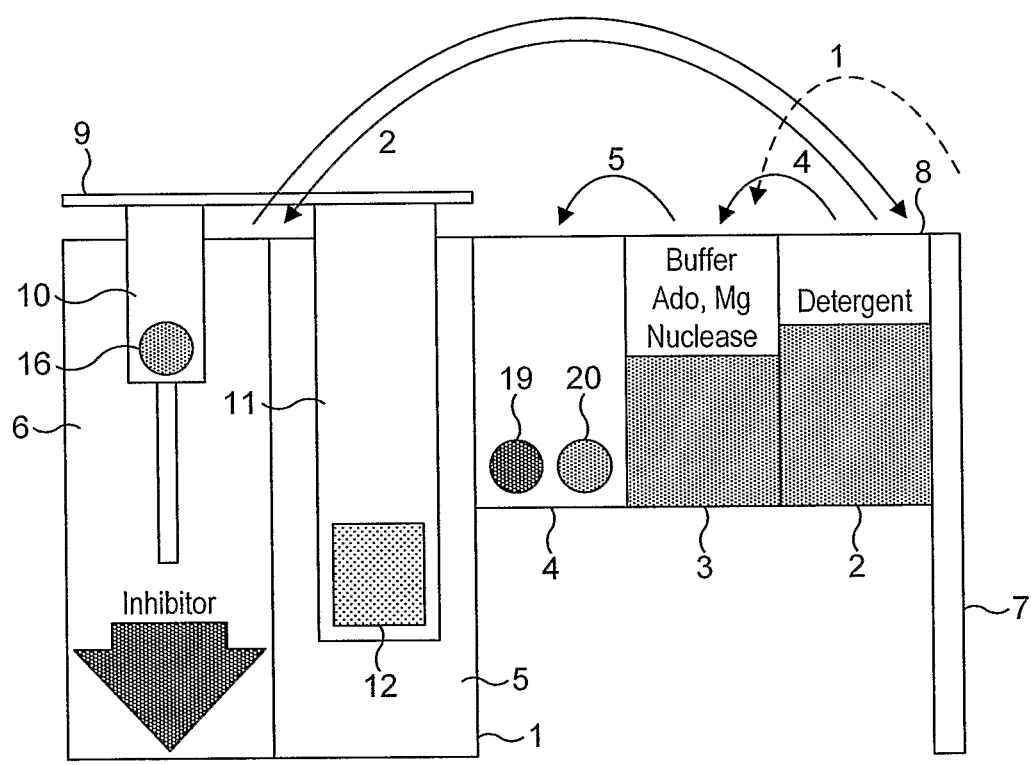

FIG. 7 is analogous to FIG. 1 except that the contents of Wells 1 to 5 are as described in Example 13 and the arrows represent the sequential material transfer set out in Example 14.

Figure 8A:
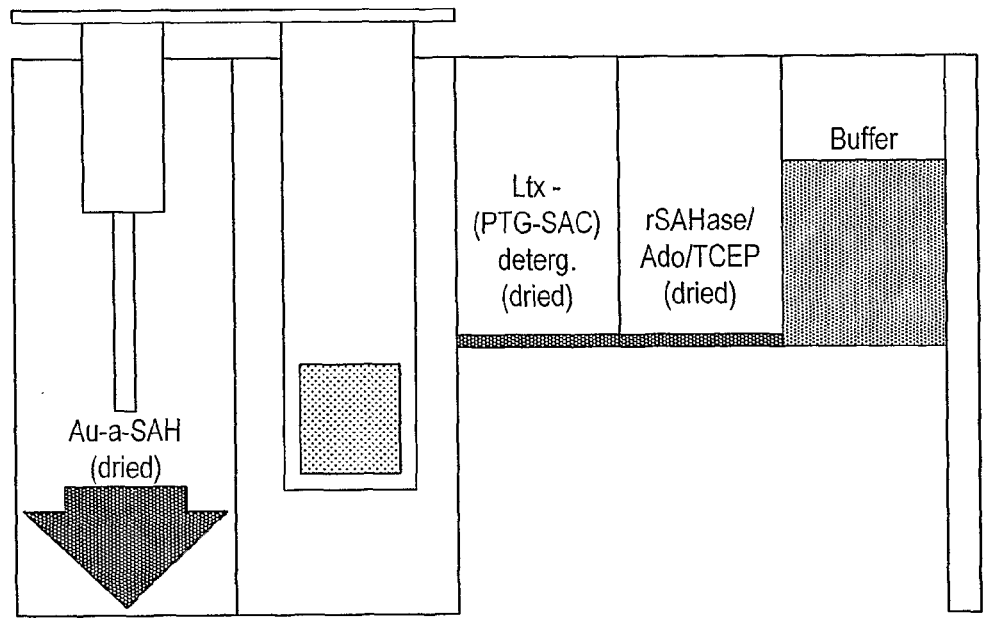
FIG. 8A shows the 5-well assay cartridge of Example 1.
Figure 8B:
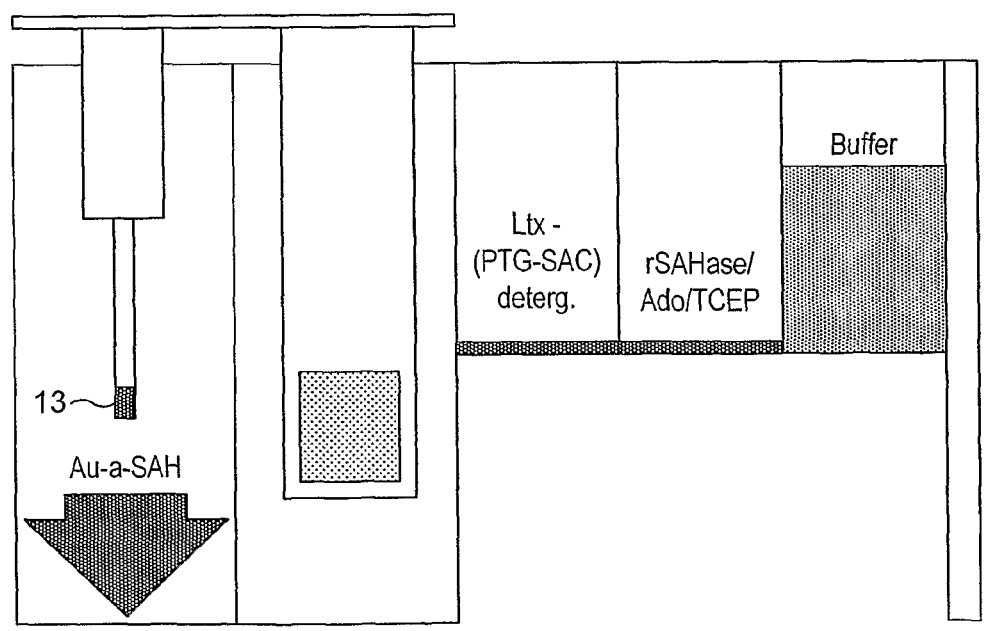
Figure 8C:
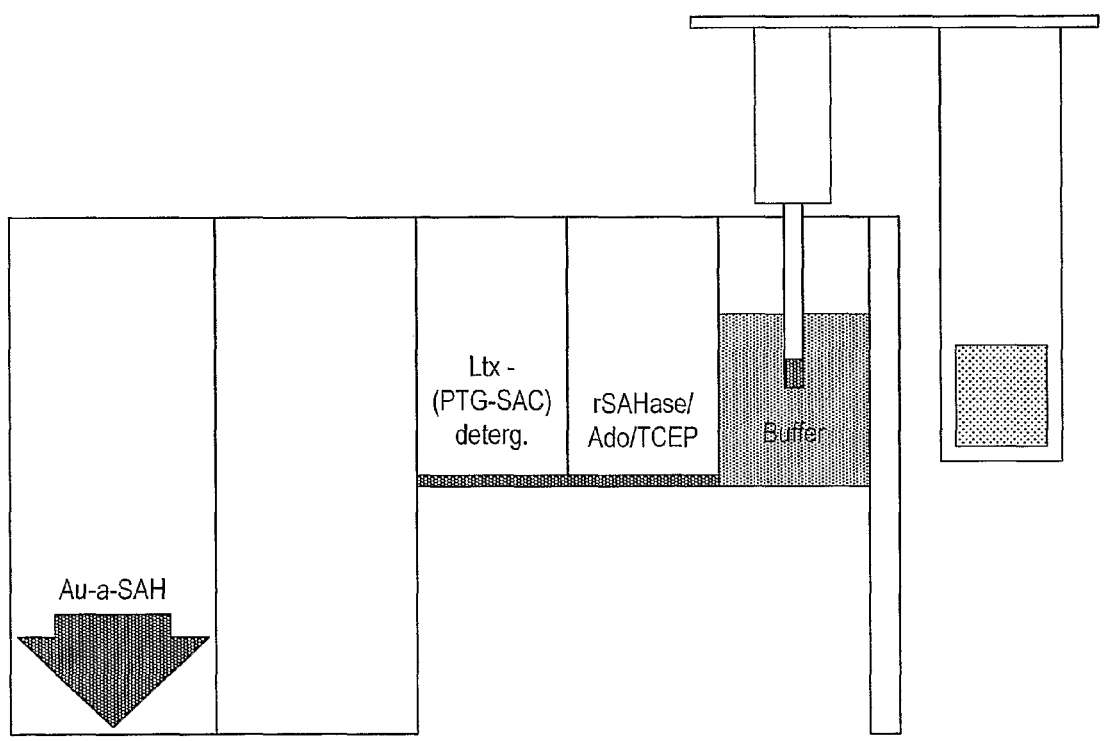
In FIG. 8C, the capillary pipette is shown moved to Well E.
Figure 8D:
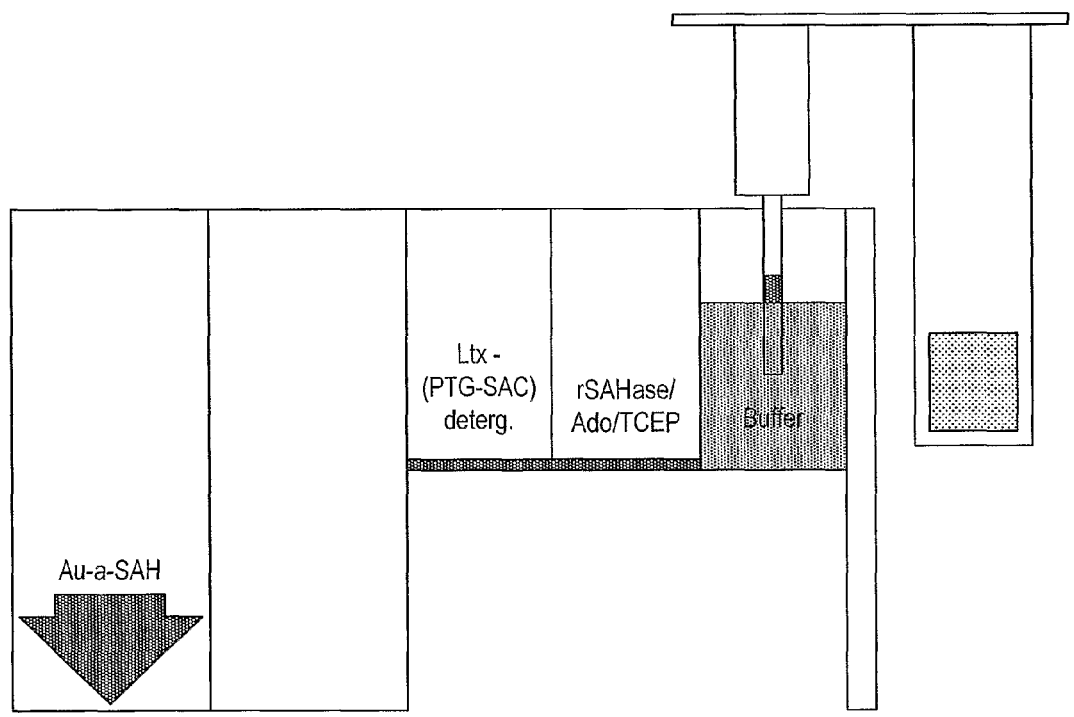
In FIG. 8D, the blood sample is diluted by uptake of 200 µL buffer from Well E.
Figure 8E:
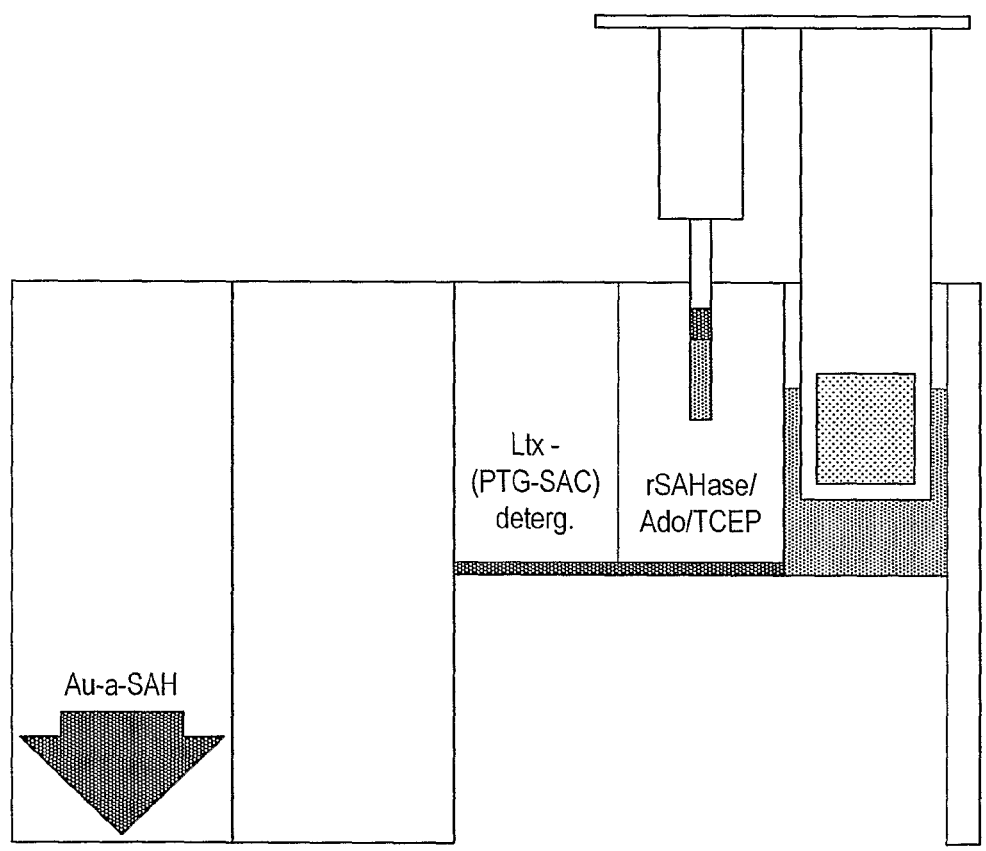
In FIG. 8E, the capillary pipette is shown moved to Well D.
Figure 8F:
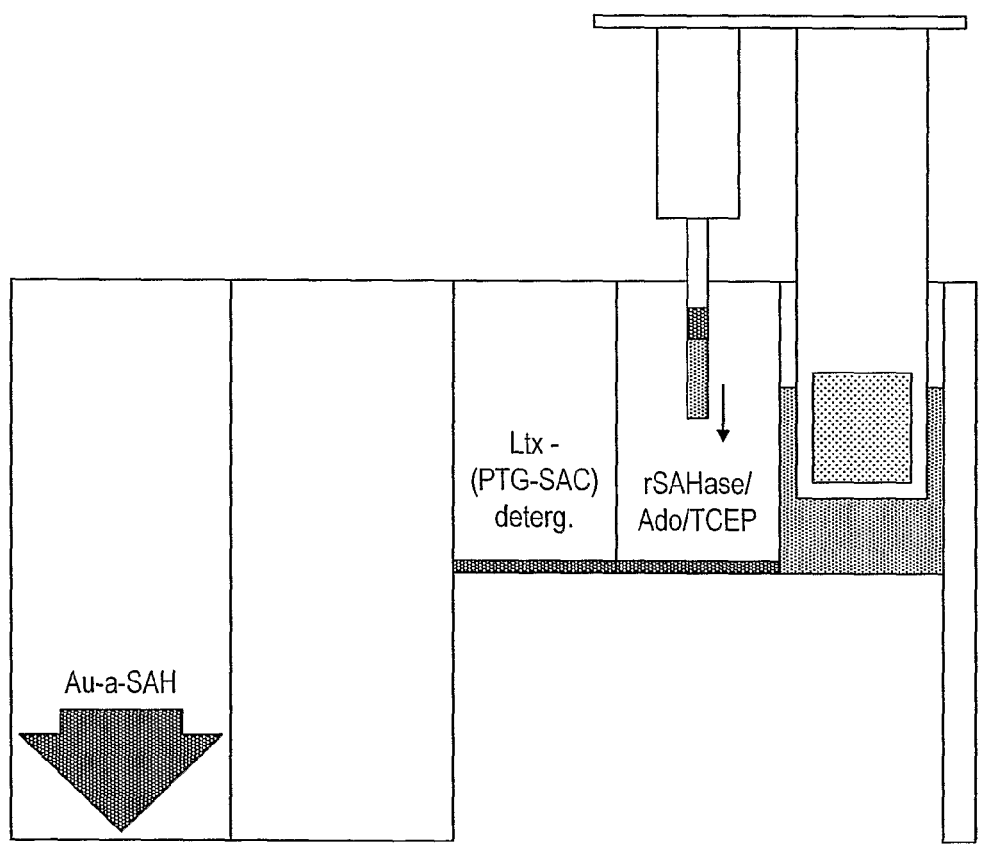
In FIG. 8F, the diluted sample is emptied into Well D.
Figure 8G:
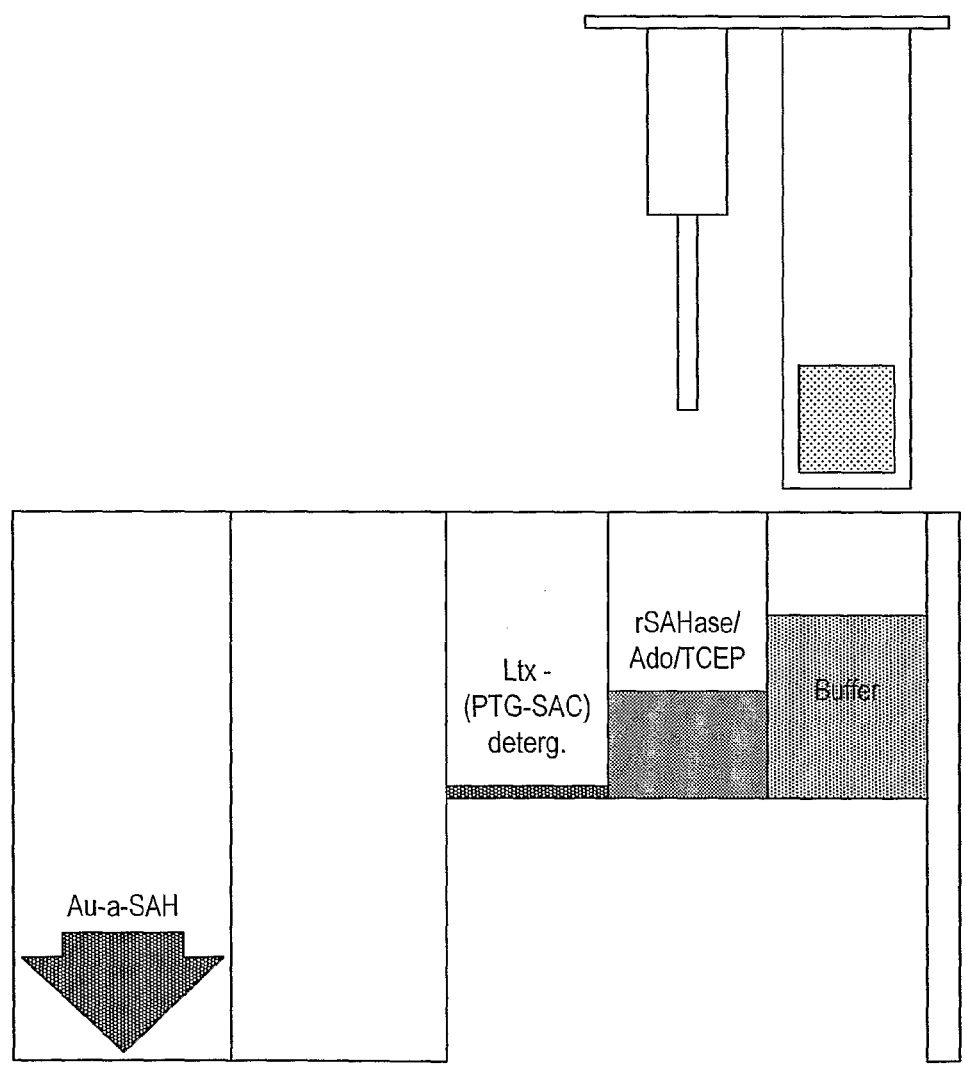
In FIG. 8G, the capillary pipette is shown removed from Well D.
Figure 8H:
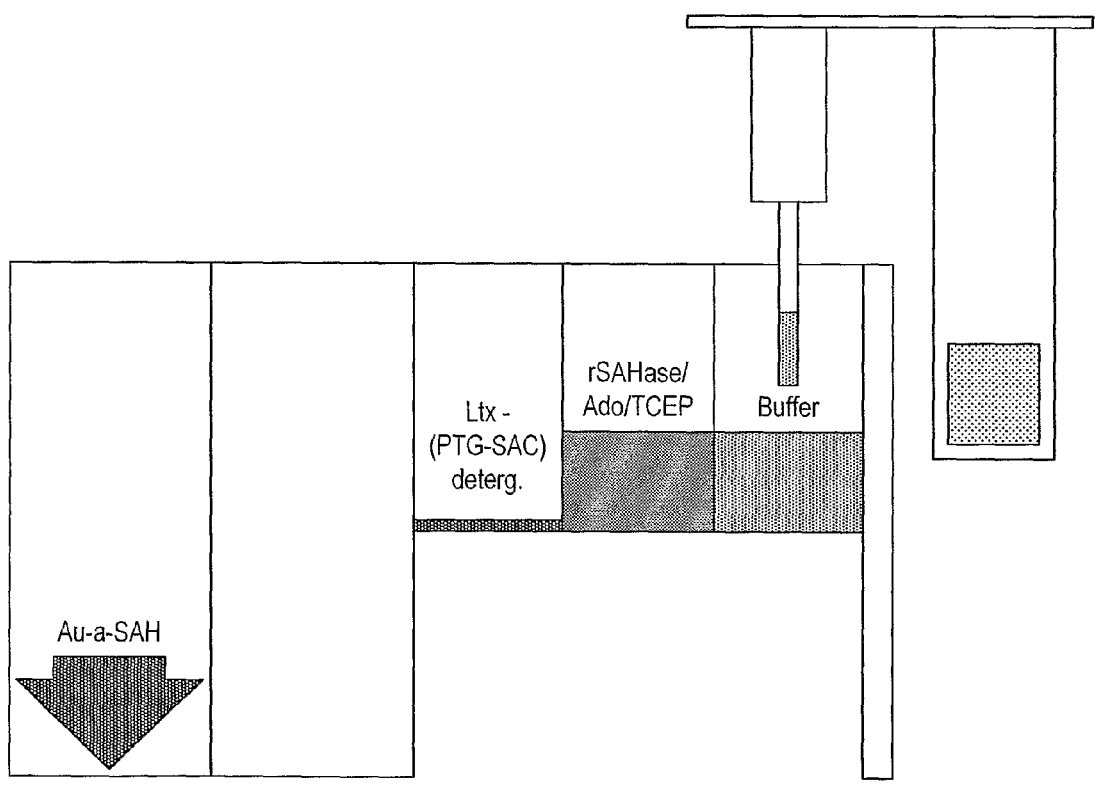
In FIG. 8H, the capillary pipette is shown taking up 85 µL of the contents of Well E.
Figure 8I:
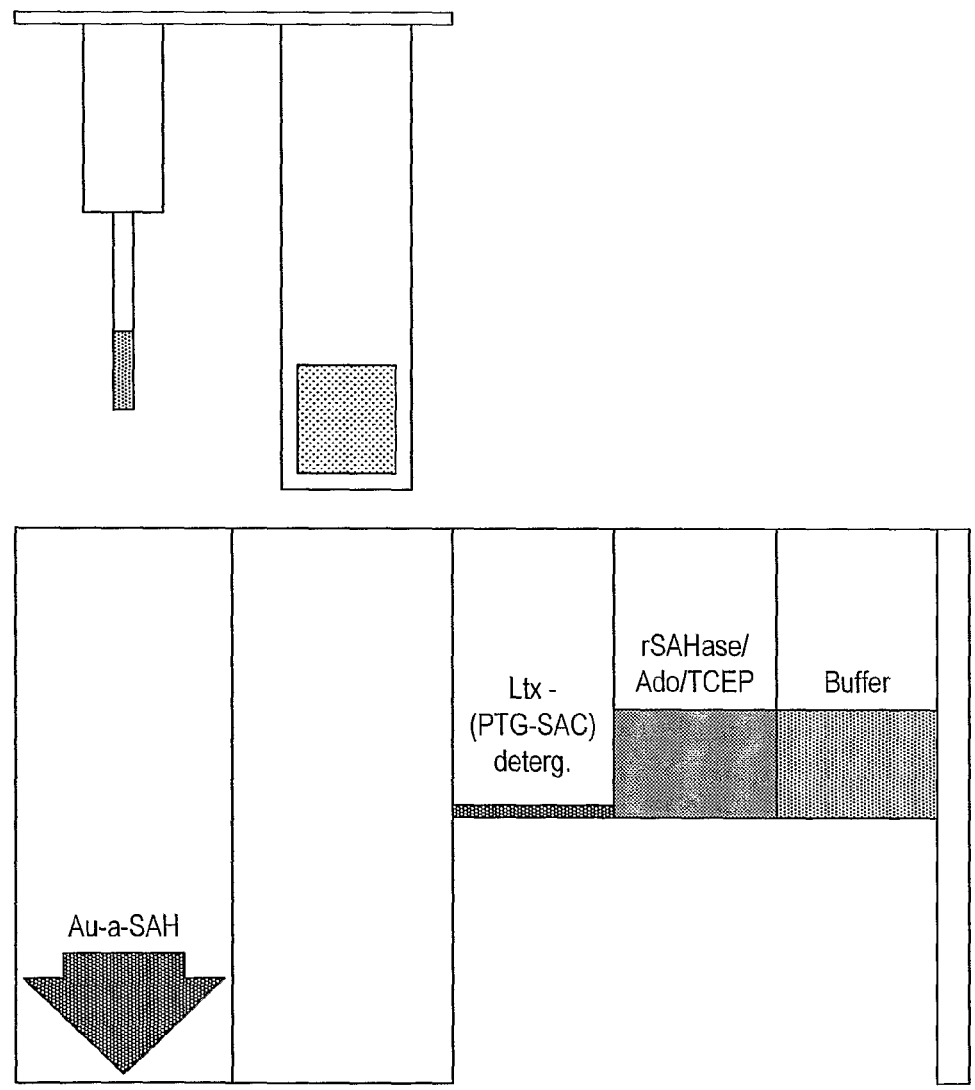
In FIG. 8I, the capillary pipette is shown removed from Well E.
Figure 8J:
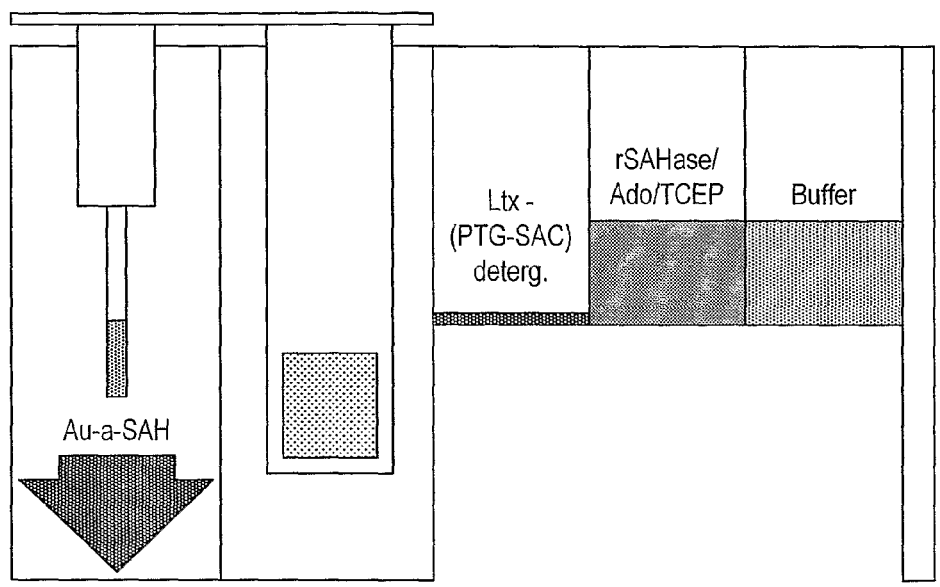
In FIG. 8J, the capillary pipette is shown moved to Well A.
Figure 8K:
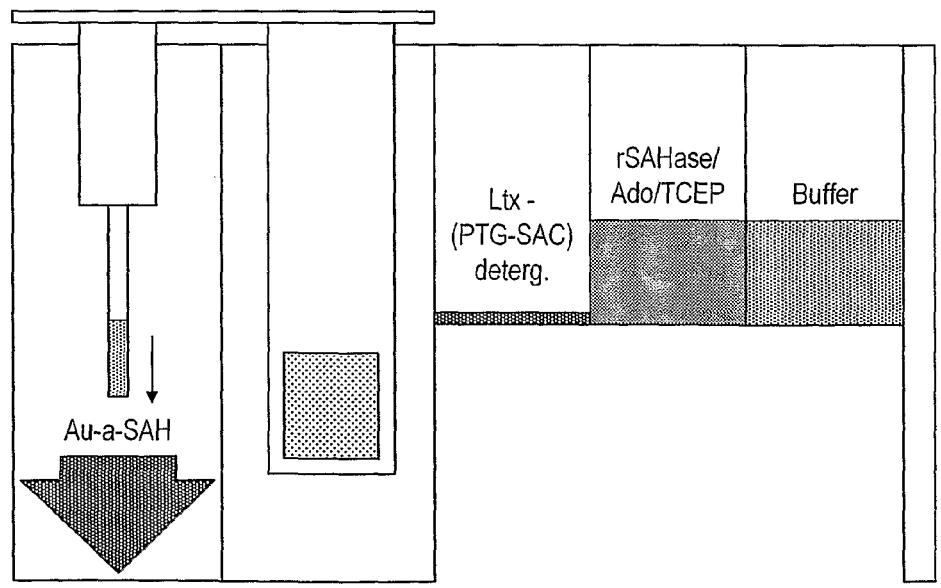
In FIG. 8K, the buffer is emptied into Well A to dissolve the gold conjugate therein.
Figure 8L:
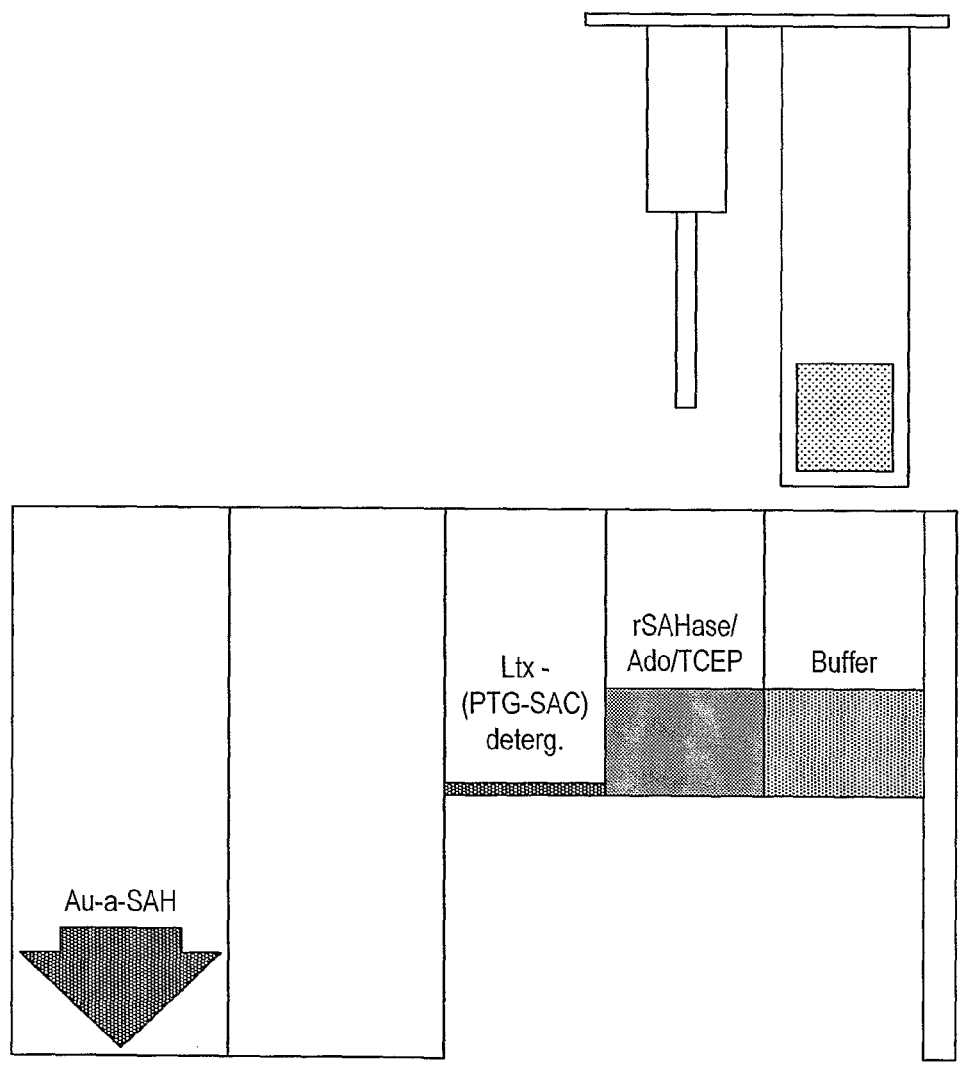
In FIG. 8L, the capillary pipette is shown removed from Well A.
Figure 8M:
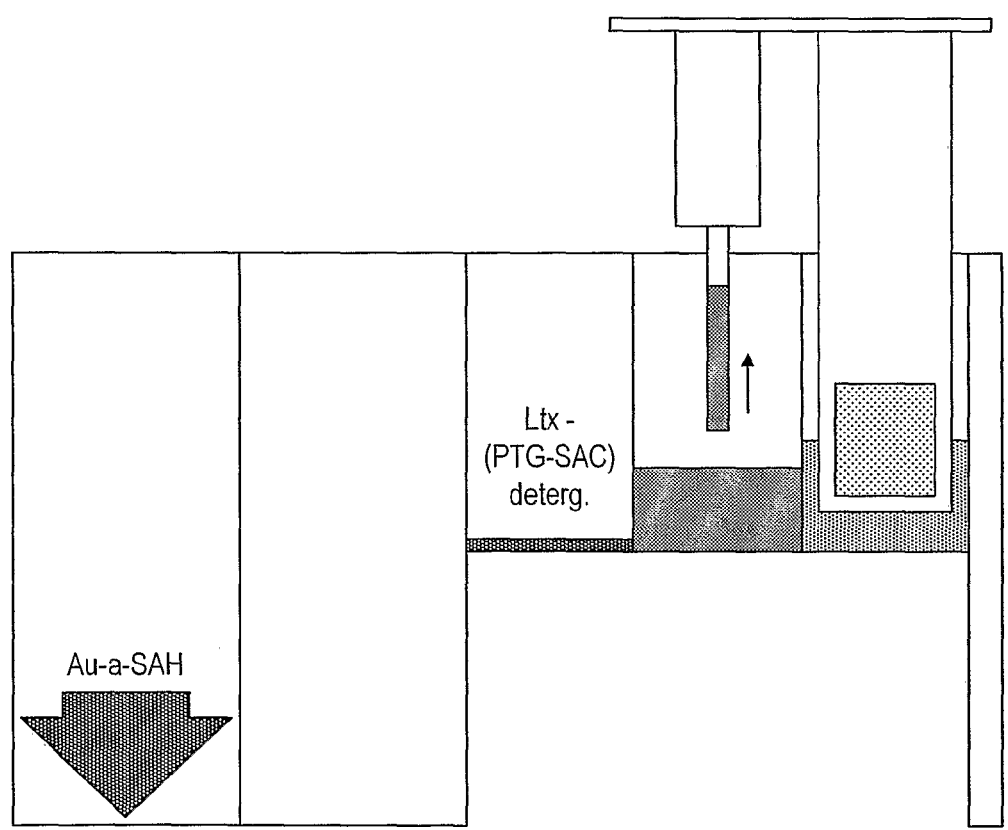
In FIG. 8M, the capillary pipette is shown taking up 100 µL of the contents of Well D.
Figure 8N:
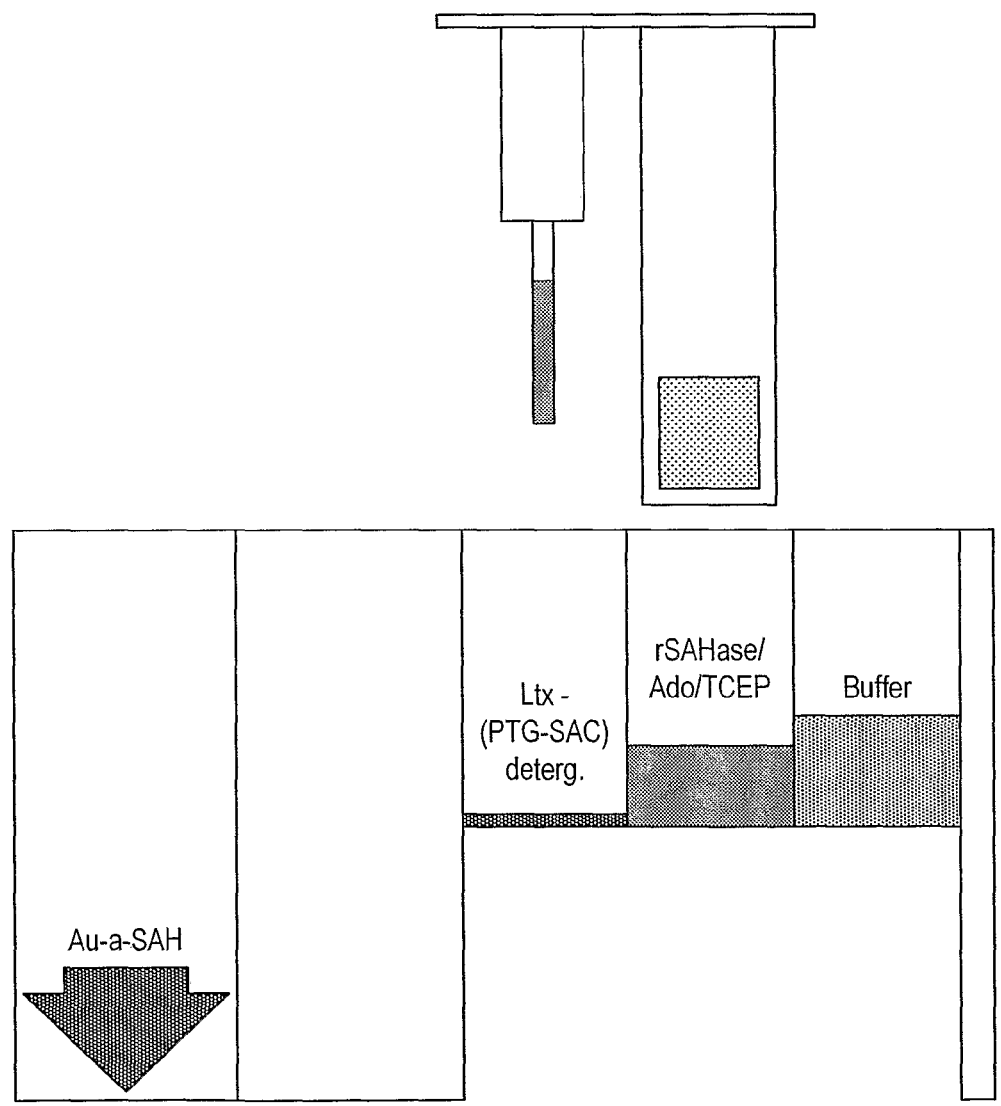
In FIG. 8N, the capillary pipette is shown removed from Well D.
Figure 8O:
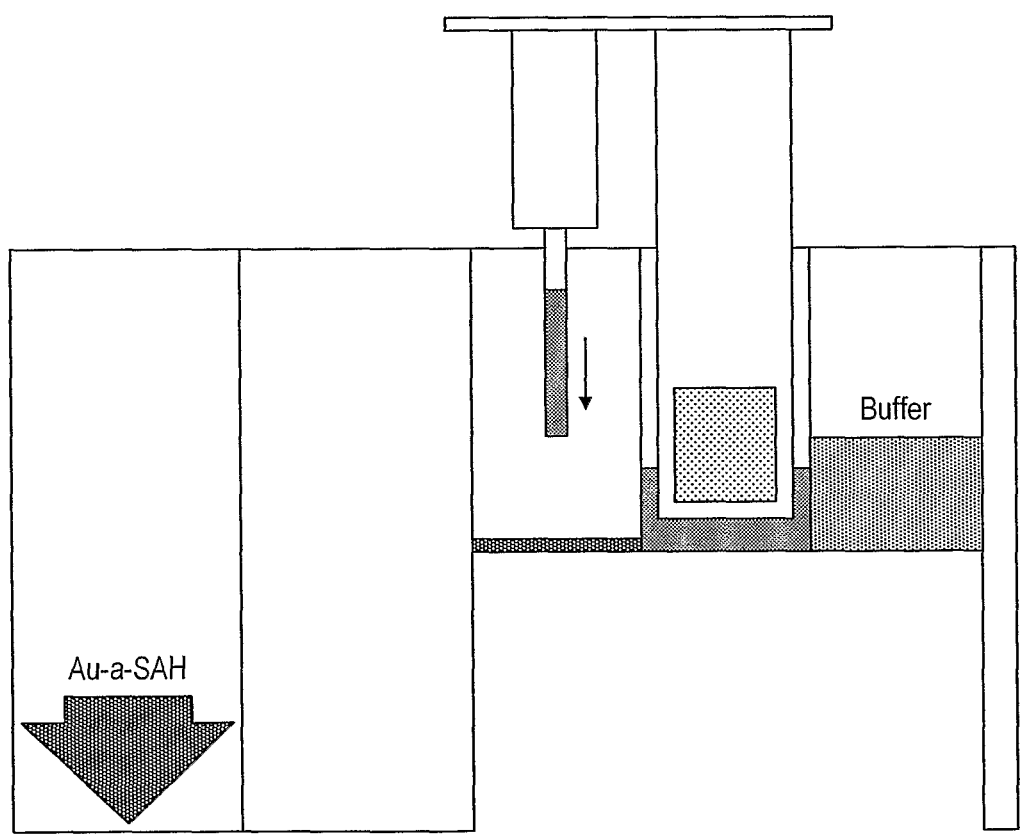
In FIG. 8O, the sample in the capillary pipette is emptied into Well C.
Figure 8P:
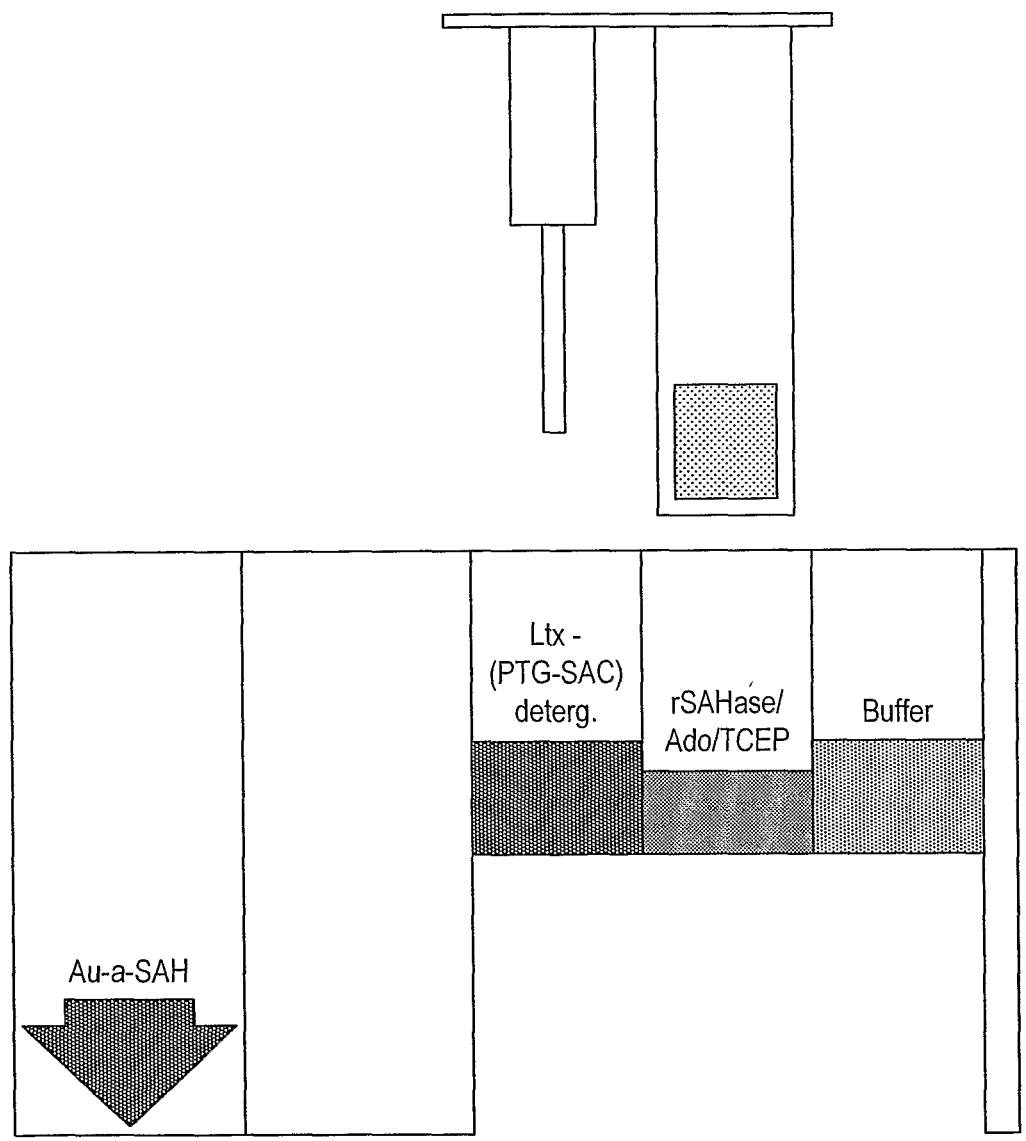
In FIG. 8P, the capillary pipette is shown removed from Well C.
Figure 8Q:
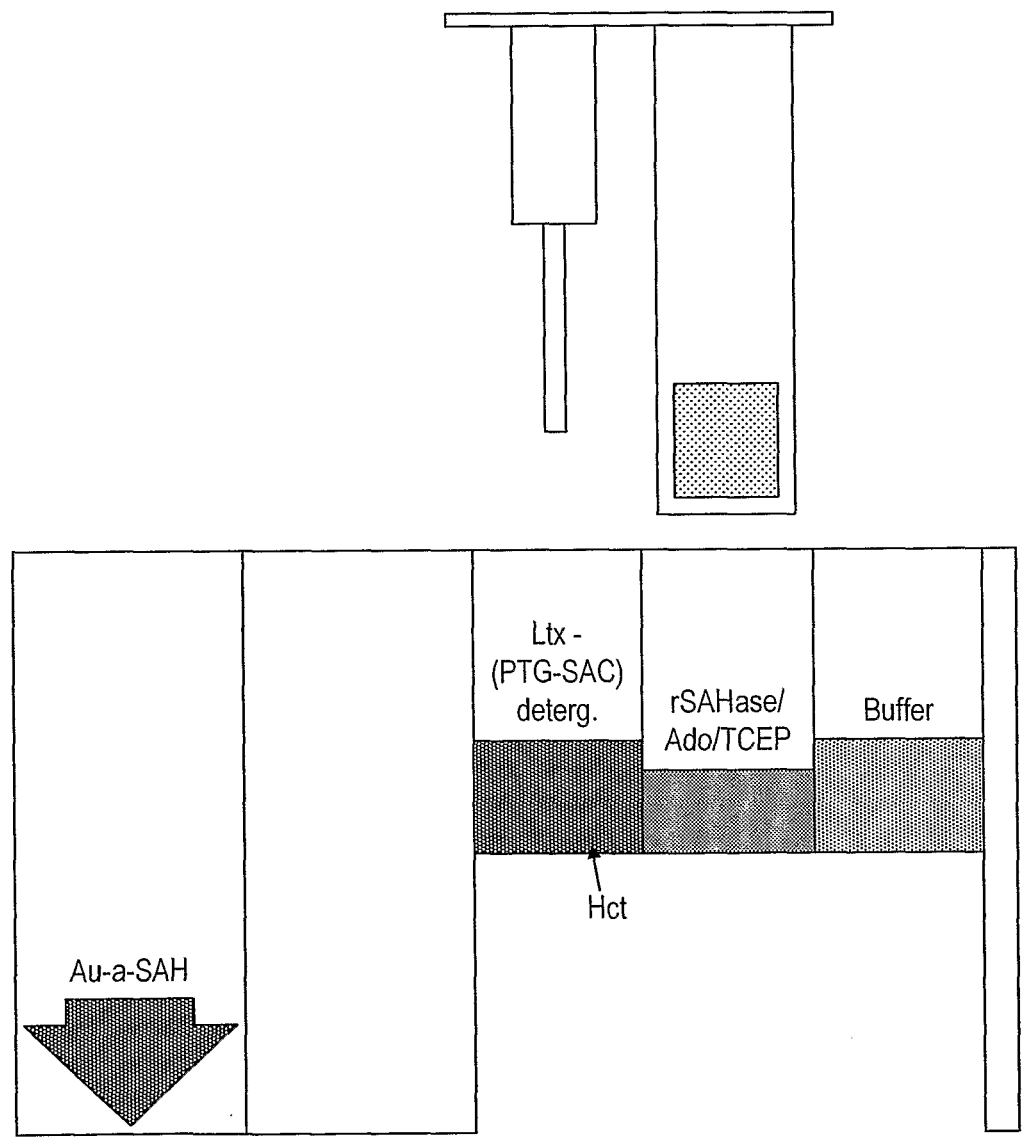
FIG. 8Q illustrates the measurement of the hematocrit level in Well C.
Figure 8R:
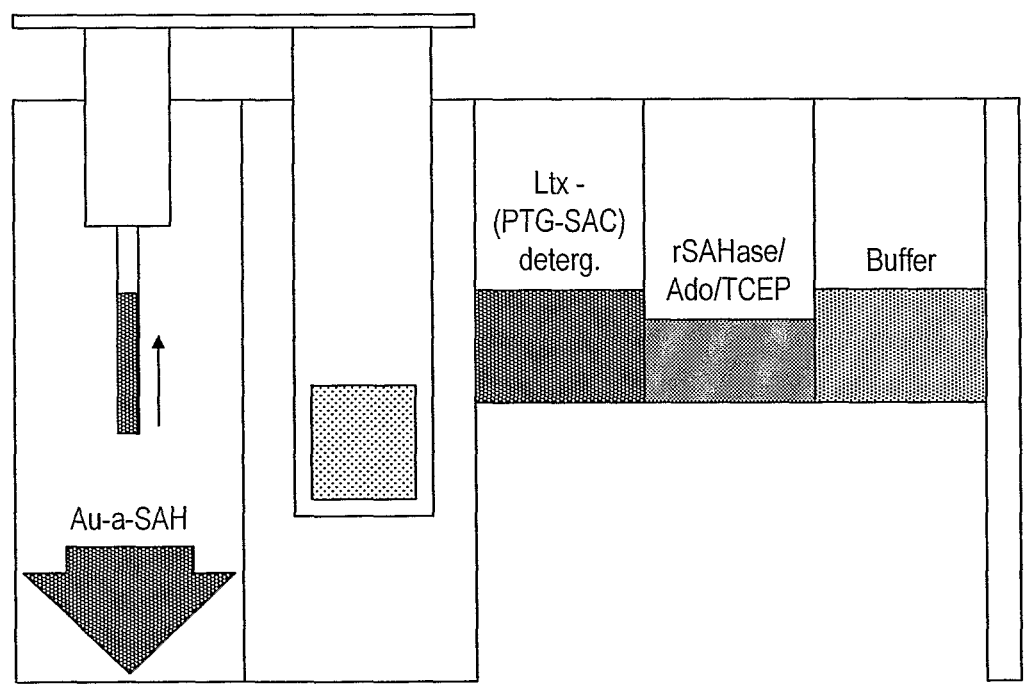
In FIG. 8R, the capillary pipette is shown taking up 60 µL of the contents of Well A.
Figure 8S:
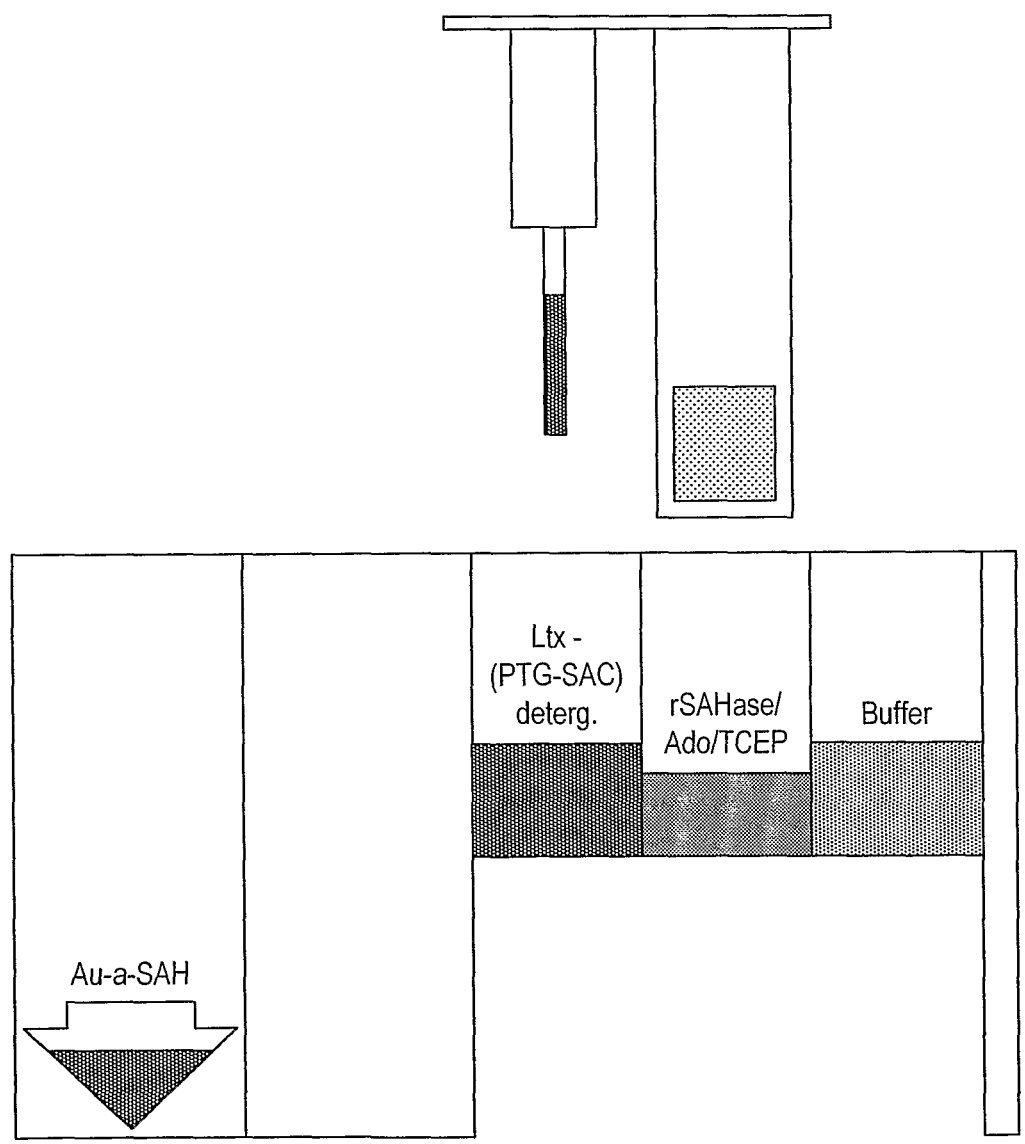
In FIG. 8S, the capillary pipette is shown removed from Well A.
Figure 8T:
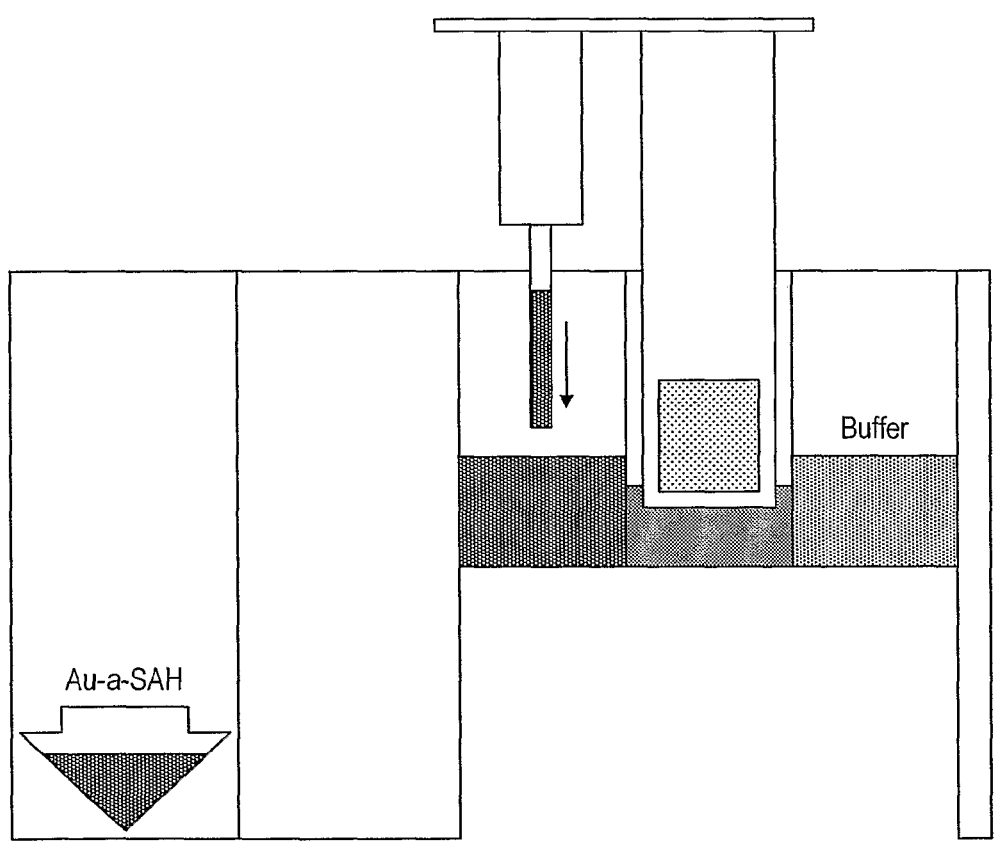
Figure 8U:
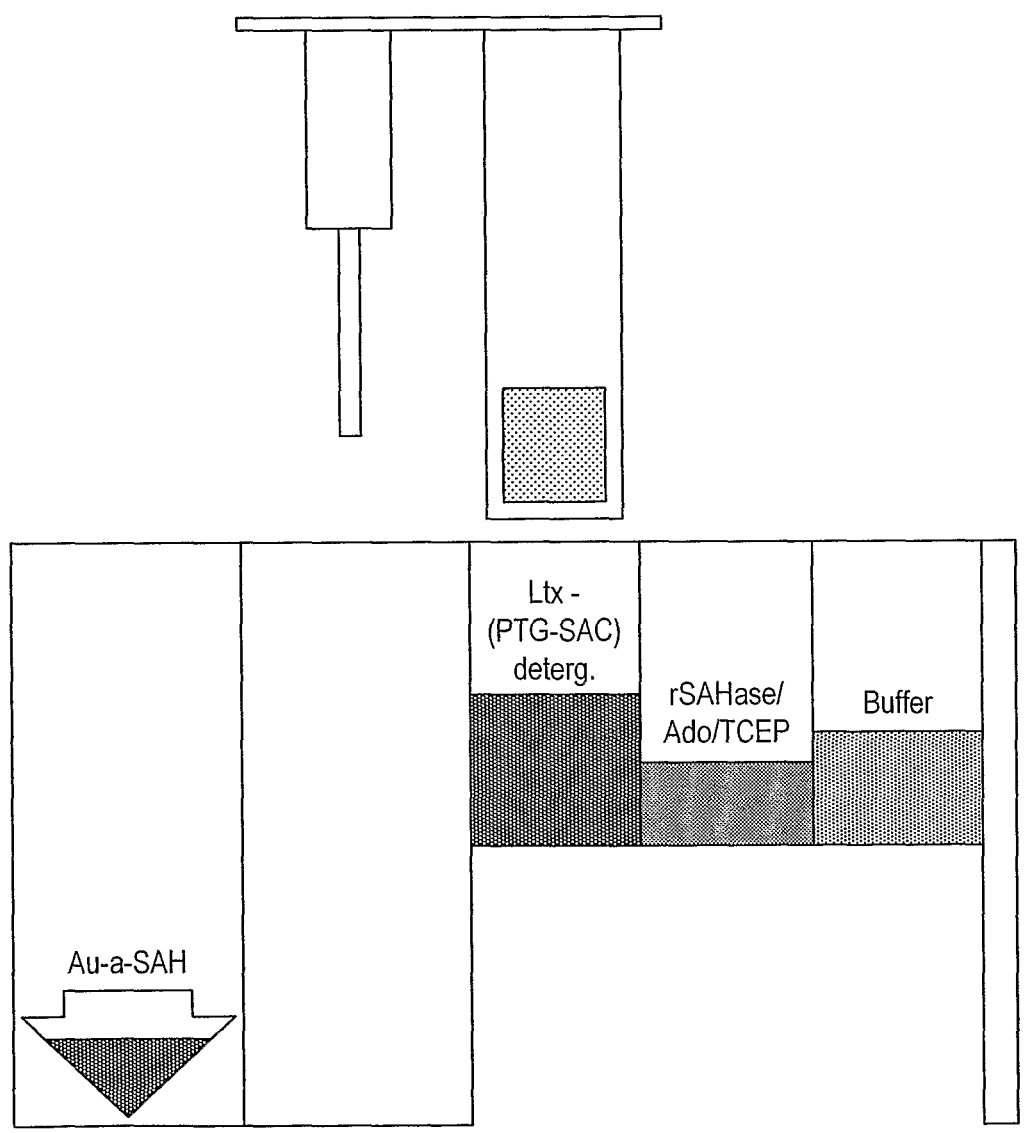
In FIG. 8U, the capillary pipette is shown removed from Well C.
Figure 8V:
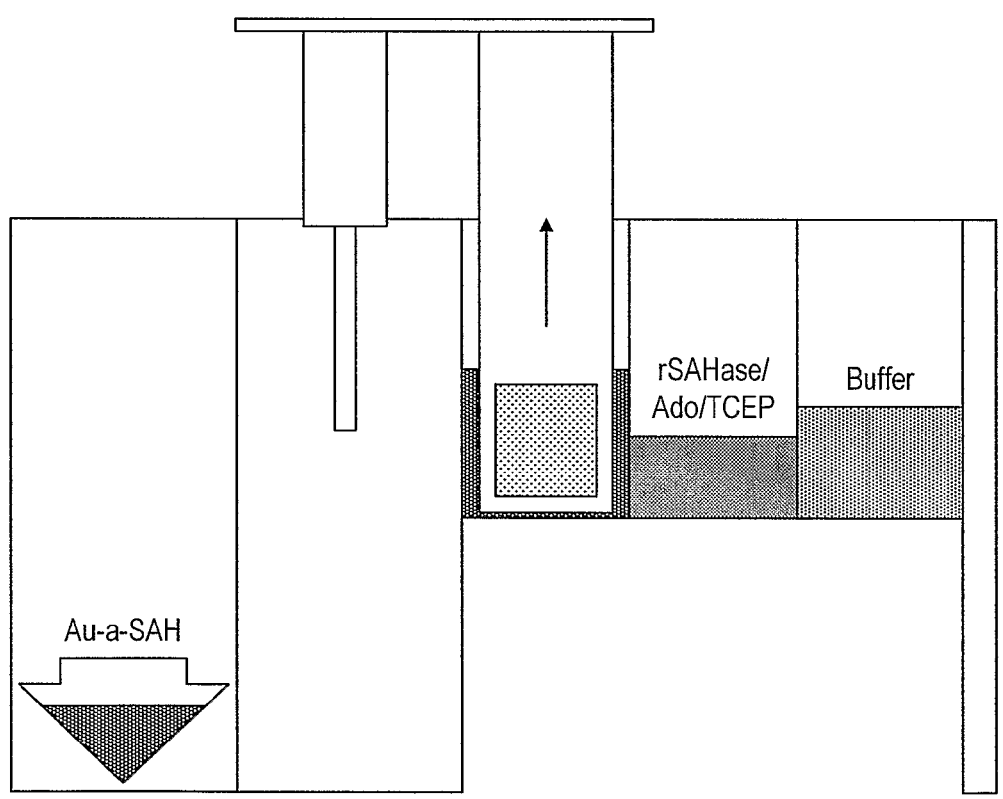
In FIG. 8V, the total contents of Well C are shown being drawn up into the membrane-tipped pipette.
Figure 8W:
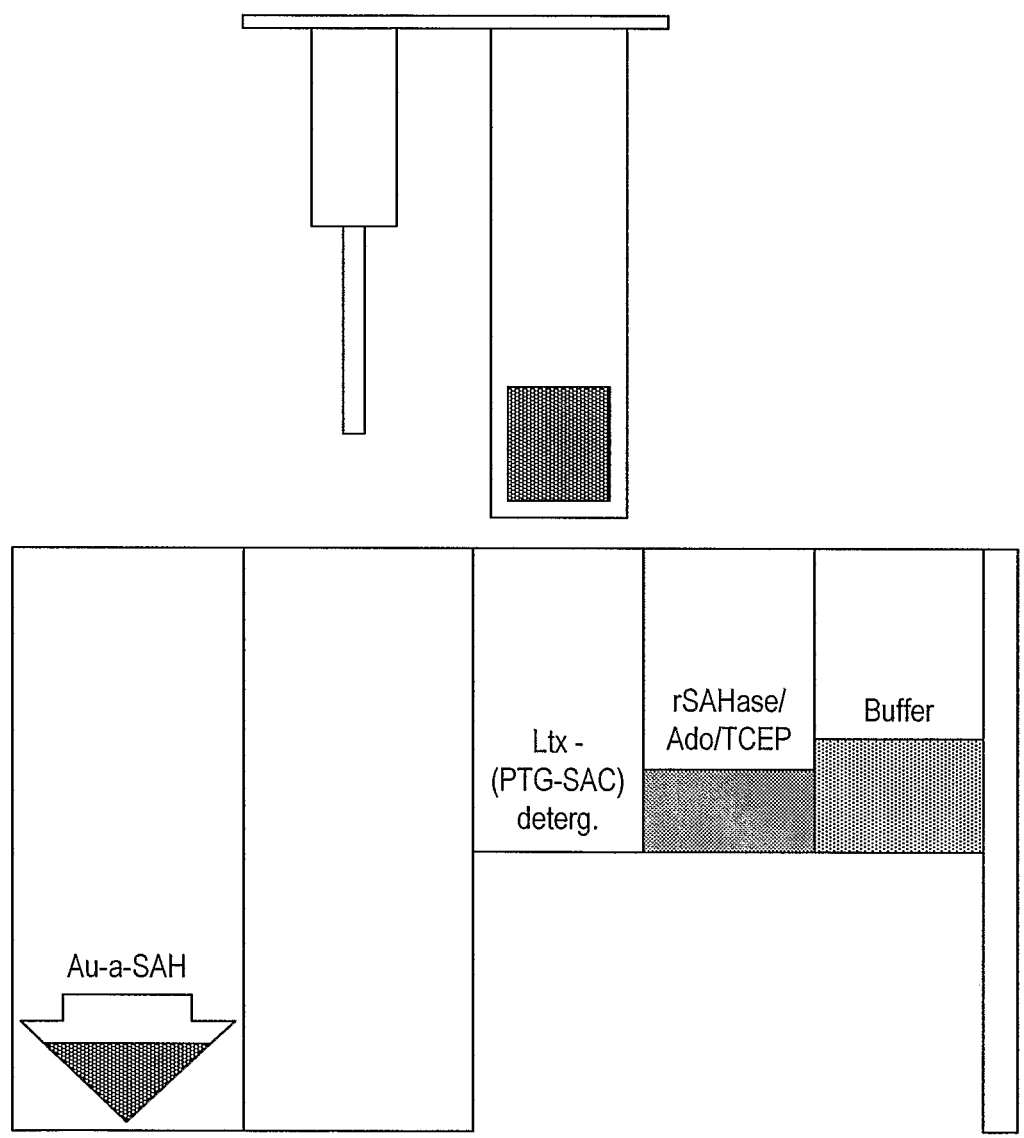
In FIG. 8W, the membrane-tipped pipette is shown removed from Well C.
Figure 8X:
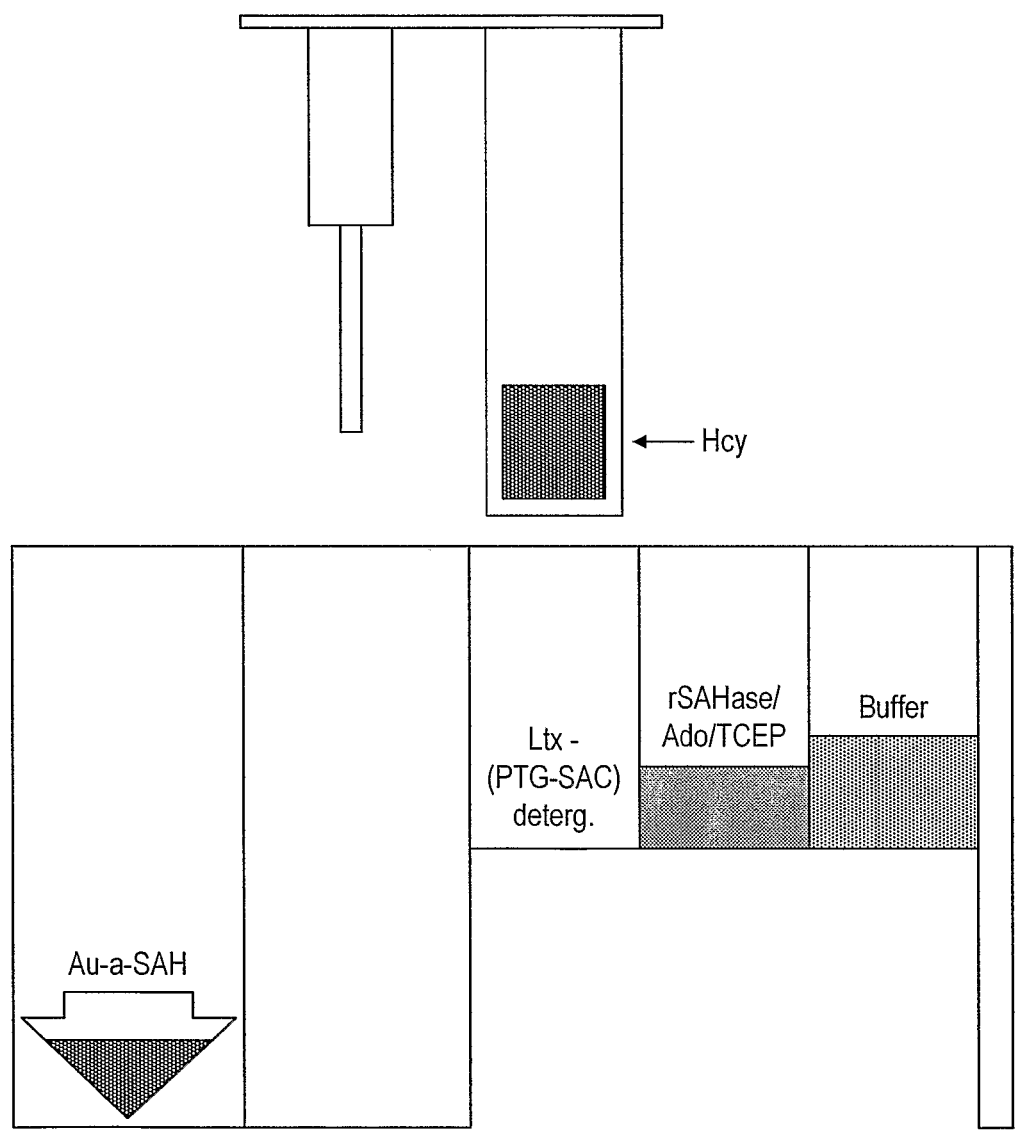
FIG. 8X illustrates gold colloid retained on the outside of the membrane (corresponding to the gold/latex conjugate formed on the second incubation) for detection and determination of Hcy content.

Referring to FIG. 8, the sequence of material transfers set out in Example 2 is shown in FIGS. 8A to 8X.

In the Examples, percentages are by weight unless otherwise stated.

EXAMPLES

Example 1

Assay Cartridge for FIG. 1

Well A

This well contains approximately 22 μg of a conjugate of colloidal gold (about 100 nm particle size) and an anti-SAH antibody prepared as described in Example 1 of WO 00/40973 and conjugated as described in U.S. Pat. No. 5,691,207 and U.S. Pat. No. 5,650,333, vacuum dried onto an inverse conical plastic cup.

Well B

This well contains a pipette tipped with a Supor 800 membrane (Pall–pore size 0.8 μm) approximately 4 mm×8 mm.

Well C

This well contains 185 μl of buffer (10 mM phosphate, 150 mM NaCl, pH 7.4 or 25 mM tris, 150 mM NaCl, pH8.1) containing an enzyme inhibitor (0.2% merthiolate) and a lysing agent (1% Triton X-100).

Well D

The well contains 0.27 μg adenosine, 50 μg particulate (1 μm latex particles conjugated to S-adenosyl-cysteine) or 300 g particulate (2 μm latex particles conjugated to S-adenosyl-cysteine), about 5 units recombinant SAH-hydrolase, and reducing agent (23 μg TCEP (tris(2-carboxyethyl)phosphine:HCl)). The well is filled with a concentrated aqueous solution of these contents and then vacuum-dried.

Well E

This well contains 300 to 350 μL of buffer (10 mM phosphate, 150 mM NaCL, pH 7.4 or 25 mM tris, 150 mM NaCl, pH8.1).

Example 2

Assay Performance for FIG. 1/Example 1

A blood sample (5 to 10 μL) in the capillary shown in Well A is diluted by uptake of 200 μL buffer from Well E and then emptied into Well D. The capillary pipette is used to transfer 85 μL of the contents of Well C to Well A to dissolve the gold conjugate. The cartridge is then incubated at 37° C. for 3 minutes before the capillary pipette is used to transfer 100 μL of the contents of Well D into Well C. The hematocrit level is then measured by detection of absorbance of light from a green or blue diode by the contents of Well C. The capillary pipette is then used to transfer 60 μL of the contents of Well A into Well C. The cartridge is then incubated at 37° C. for 1 minute. The total contents of Well C are then drawn up into the membrane-tipped pipette (optionally followed by the remaining buffer in Well E) to reduce background. The gold colloid retained on the outside of the membrane (corresponding to the gold/latex conjugate formed on the second incubation) is then detected in reflection mode using green or blue diode illumination.

The assay is calibrated using standards of known HCy content and hematocrit determination is likewise calibrated against standard, e.g. centrifugal, hematocrit determination for a series of blood samples.

Example 3

Assay Cartridge for FIG. 2

Well A

As in Example 1, but approximately 22 μg conjugate.

Well B

As in Example 1.

Well C

This well contains 0.27 μg adenosine, 20 μg particulate (1 μm latex particles conjugated to S-adenosyl-cysteine) or 160 μg particulate (2 μm latex particles conjugated to S-adenosyl-cysteine), about 5 units recombinant SAH-hydrolase, and reducing agent (23 kg tris(2-carboxyethyl)phosphine:HCl). The well is filled with a concentrated aqueous solution of these contents and then vacuum-dried.

Well D

This well contains 225 μL buffer (10 mM phosphate, 150 mM NaCl, pH 7.4 or 25 mM tris, 150 mM NaCl, pH 8.1) containing an enzyme inhibitor (0.4% merthiolate) and a lysing agent (2% Triton X-100).

Well E

This well contains 350 μL buffer (10 mM phosphate, 150 mM NaCl, pH 7.4 or 25 mM tris, 150 mM NaCl, pH 8.1).

Example 4

Assay Performance for FIG. 2/Example 3

A blood sample (5-10 μL) taken into the capillary pipette is diluted by withdrawing 160 μL of buffer from Well E into the capillary pipette. The capillary pipette contents are then expelled into Well C. 85 μL of buffer from Well E (or alternatively Well D) is transferred into Well A using the capillary pipette. The cartridge is then incubated at 37° C. for 3 minutes. 40 μL of the contents of Well D are then transferred into Well C using the capillary pipette. The hematocrit value is then determined as in Example 2 using the contents of Well C. 60 μL of the contents of Well A is transferred to Well C using the capillary pipette and the cartridge is incubated at 37° C. for 1 minute. The contents of Well C (optionally followed by the remaining contents of Wells D and/or E) are taken up into the membrane-tipped pipette and the gold colloid retained on the outside of the membrane is measured as in Example 2. Calibration is effected as in Example 2.

Example 5

Assay Cartridge for FIG. 3

Well A

As in Example 1.

Well B

As in Example 1.

Well C

This well contains 20 μg particulate (1 μm latex particles conjugated to S-adenosyl-cysteine) or 160 μg particulate (2 μm latex particles conjugated to S-adenosyl-cysteine), 75 μg merthiolate, and 750 μg Triton X-100. The well is filled with a concentrated aqueous solution of these components and then vacuum-dried.

Well D

This well contains 0.27 μg adenosine, 5 units recombinant SAH-hydrolase, and 23 μg TCEP:HCl. The well is filled with a concentrated aqueous solution of these components and then vacuum-dried.

Well E

This well contains 350 μL buffer (10 mM phosphate, 150 mM NaCl, pH 7.4 or 25 mM tris, 150 mM NaCl, pH 8.1).

Example 6

Assay Performance for FIG. 3/Example 5

A blood sample (5 to 10 μL) in the capillary pipette is diluted by uptake of 175 μL of the buffer from Well E and expelled into Well D. 80 µL of buffer from Well E are then transferred into Well A using the capillary pipette. The cartridge is then incubated at 37° C. for 3 minutes. 75 µL of the contents of Well D are then transferred to Well C using the capillary pipette. The hematocrit value is then determined as in Example 2 using the contents of Well C. 50 L of the contents of Well A are then transferred into Well C using the capillary pipette. The cartridge is then incubated at 37° C. for 1 minute. The contents of Well C (optionally followed by the contents of Well E) are then taken up into the membrane-tipped pipette and the gold colloid retained on the outside of the membrane is then measured as in Example 2. Calibration is effected as in Example 2.

Example 7

Assay Cartridge for FIG. 4

Well A
As in Example 3.
Well B
As in Example 1.
Well C
The contents of this well are 60 µL of an aqueous composition containing 4.5 µg/ml adenosine, 330 µg/mL particulate (1 µm latex particles conjugated to S-adenosyl-cysteine) or 2.7 mg/mL (2 µm latex particles conjugated to S-adenosyl-cysteine), 80 U/mL recombinant SAH-hydrolase, and 380 µg/mL TCEP:HCl.
Well D
This well contains 225 µL buffer (10 mM phosphate, 150 mM NaCl, pH 7.4 or 25 mM tris, 150 mM NaCl, pH 8.1) containing 0.4% merthiolate and 2% Triton X-100.
Well E
This well contains 285 µL buffer (10 mM phosphate, 150 mM NaCl, pH 7.4 or 25 mM tris, 150 mM NaCl, pH 8.1)

Example 8

Assay Performance for FIG. 4/Example 7

A blood sample (5 to 10 µL) in the capillary pipette is diluted by uptake of 100 µL buffer from Well E and expelled into Well C. 85 µL of buffer from Well E (or Well D) is then transferred into Well A using the capillary pipette. The cartridge is then incubated at 37° C. for 3 minutes. 40 µL of the contents of Well D are then transferred to Well C and hematocrit is subsequently measured as in Example 2. 60 µL of the contents of Well A is then transferred into Well C using the capillary pipette and the cartridge is incubated at 37° C. for 1 minute. The contents of Well C (optionally followed by the contents of Wells D and/or E) are taken up into the membrane-tipped pipette and the gold colloid retained on the outside of the membrane is then measured as in Example 2. Calibration is effected as in Example 2.

Example 9

Assay Cartridge for FIG. 5

Well A
This well contains an absorbent wiper 15 which serves to remove any excess sample from the tip of capillary-tipped pipette 10 when this is placed in the cartridge 1. Within the body of pipette 10 are disposed reagent containing beads 16 and 17. Bead 16 contains approximately 5 units of rSAHase together with 65 µg of TCEP. Bead 17 contains about 0.1 units of nuclease (e.g. Benzonase from Merck) together with 40 µg MgCl$_2$. Both beads also contain trehalose as a binder.
Well B
This well is as described in Example 1 but contains within the body of the pipette a reagent-containing bead 18 containing 120 µg N-ethyl-maleimide.
Well C
This well contains two reagent-containing beads, 19 and 20. Bead 19 contains approximately 100 µg of a gold conjugate as described for Well A in Example 1. Bead 20 contains 0.12 kg of particulate (1-2 µm, preferably 1.6 µm, latex particles conjugated to S-adenosyl-cysteine as described for Well D in Example 1).
Well D
This well contains 0.27 kg adenosine in 200 µL of buffer (10 mM phosphate, 150 mM NaCl, pH 7.4 or 25 mM tris, 150 mM NaCl, pH 8.1).
Well E
This well contains 300 µL 0.4% wt. SDS in the buffer of Well D.

Example 10

Assay Performance for FIG. 5/Example 9

With 4.5 µL blood sample (3 to 10 µL) in the capillary shown in Well A, 200 µL buffer (125-300 µL) are taken up from Well D into the capillary-tipped pipette to dissolve beads 16 and 17.
The contents are flushed back into Well D and incubated at 37° C. for 1 minute (up to 3 minutes).
During that incubation, 200 µL detergent solution (125-300 µL) from Well E is drawn into the membrane-tipped pipette to dissolve bead 18. The contents are then flushed back into Well E.
100 µL detergent and inhibitor solution (25-200 µL) are then transferred from Well E into Well D using the capillary-tipped pipette. After erythrocyte lysis, the hemotocrit is determined in Well D as in Example 2.
200 µL of the mixture (150-275 µL) in Well D is then transferred from Well D into Well C using the capillary-tipped pipette, beads 19 and 20 are allowed to dissolve and the mixture is incubated for 1 minute (up to 3 minutes).
The total contents of Well C are then drawn up into the membrane-tipped pipette, optionally followed by the remaining buffer in Well E. The gold colloid retained on the outside of the membrane (corresponding to the gold/latex conjugate formed on the second incubation) is then detected in reflection mode using green or blue diode illumination.
The assay is calibrated using standards of known HCy content and hematocrit determination is likewise calibrated against standard, e.g. centrifugal, hematocrit determination for a series of blood samples.
Volume or quantity ranges in brackets are optional limits for amounts transferred. However for accurate assay performance and calibration a predetermined value within these ranges should be used.

Example 11

Assay Cartridge for FIG. 6

Well A
This is as described in Example 9 but omits bead 17.
Well B
This is as described in Example 9.

Well C

This is as described in Example 9.

Well D

This is as described in Example 9 but also contains 0.1 units of nuclease (as described in Example 9 for Well A) and 40 µg MgCl$_2$.

Well E

This is as described in Example 9.

Example 12

Assay Performance for FIG. 6/Example 11

The steps of the assay are performed as described in Example 10.

Example 13

Assay Cartridge for FIG. 7

Well A

The capillary-tipped pipette and the bead (16) within it are as described in Example 11. The base of the well contains an insert (as described in Example 1) containing a dried inhibitor composition containing 80-200 µg, e.g. 120 µg of N-ethyl-maleimide.

Well B

This is as described in Example 1.

Well C

This is as described in Example 9.

Well D

This is as described in Example 11.

Well E

This is as described in Example 9.

Example 14

Assay Performance for FIG. 7/Example 13

The sample and the enzyme and reducing agent are transferred to Well D and incubated therein as in Example 10.

During this incubation, 50 µL of detergent solution (40-100 µL) are transferred into Well A from Well E using the capillary-tipped pipette. This mixture is then transferred back into Well E.

Detergent and inhibitor are then transferred to Well D as in Example 10 and the assay is continued as in Example 10.

Example 15

Reagent Beads

The beads used in Examples 9 to 14 above are prepared as follows:

An aqueous solution of reagent(s), trehalose, polyethylene glycol (PEG), bovine serum albumin (BSA) in 25 mM Tris buffer, 150 mM NaCl, pH 7.5 is dropped using a pipette onto a cold (<−50° C.) metal plate. The frozen droplets are freeze dried to yield beads containing 15% wt. trehalose, 0.5% wt. PEG and 0.1% wt. BSA. Droplet size is conveniently 5 to 100 µL, preferably 10-50 µL.

Alternatively the solution may be added dropwise to liquid nitrodgen whereafter the frozen droplets are collected and freeze dried.

The invention claimed is:

1. A method of assaying for plasma homocysteine in a whole blood sample taken from a human or vascularized non-human animal subject, said method comprising:

contacting a whole blood sample from said subject with the following reagents—a liquid diluent, a reducing agent, a homocysteine-converting enzyme, an inhibitor of the homocysteine converting reaction of said enzyme, adenosine or an adenosine analog as homocysteine co-substrate, a cell-lysing agent, a color-labeled binding agent comprising an anti-S-adenosyl-homocysteine (SAH) antibody capable of binding to a conversion product of said homocysteine-converting enzyme, and a particulate comprising polymer particles conjugated to S-adenosyl cysteine capable of competing with said conversion product for binding to said color-labeled binding agent;

following contact with said reagents, drawing said sample through a membrane having a porosity sufficient to allow passage therethrough of said color-labeled binding agent in its unbound state and when bound to said conversion product but insufficient to allow passage therethrough of said color-labeled binding agent when bound to said particulate;

detecting the color-label of said color-labeled binding agent retained on said membrane;

determining therefrom an indication of the plasma homocysteine concentration by applying a correction factor dependent on red blood cell concentration in said whole blood sample; and optionally presenting the plasma homocysteine concentration as a visible or electronic signal;

wherein contact with said reagents is sequential or simultaneous subject to the provisos that:

i) contact with said color-labeled lysing agent occurs after contact with said diluent, enzyme and reducing agent;

ii) contact with said color-labeled binding agent and said particulate does not involve contact with a liquid containing both said color-labeled binding agent and said particulate; and iii) contact with said inhibitor occurs after contact with said diluent, enzyme and reducing cell agent and no later than contact with said cell lysing agent.

2. The method of claim 1, wherein, prior to drawing said sample a through said membrane, DNA in said sample is fragmented with a nuclease.

3. The method of claim 1, wherein at least one of the reagents is provided in bead form.

4. The method of claim 1, wherein said color-labeled binding agent is a metal-bead-labeled binding agent.

5. A single-use cartridge for a plasma homocysteine assay using whole blood, said cartridge comprising:

a multi-welled base, a removable capillary-tipped pipette, and a cover, said cover carrying a membrane-tipped pipette, and the wells of said base containing the following assay reagents: a liquid diluent; a reducing agent; a homocysteine-converting enzyme; an inhibitor of the homocysteine converting reaction of said enzyme; adenosine as homocysteine co-substrate for the catalysis of homocysteine; a cell-lysing agent; a color-labeled binding agent comprising a color-labeled anti-S-adenosyl-homocysteine (SAH) antibody; and a particulate comprising polymer particles conjugated to S-adenosyl cysteine capable of competing with SAH for binding to said color-labeled binding agent; said color-labeled binding agent and said particulate being in different said wells; said inhibitor and said enzyme being in different said wells; and said cell lysing agent being in a well different from the well or wells containing said enzyme and at least part of said reducing agent and said diluent.

6. The cartridge of claim 5, wherein said cartridge comprises at least five wells in a linear array in said base.

7. The cartridge of claim 5, wherein said cartridge comprises at least one reagent-containing bead in at least one well in said base.

8. The cartridge of claim 7, wherein said cartridge comprises at least one said bead within at least one of said pipettes.

9. The cartridge of claim 5, wherein said cartridge comprises a nuclease in at least one of the wells in said base.

10. The method of claim 2, wherein at least one of the reagents is provided in bead form.

11. The method of claim 2, wherein said color-labeled binding agent is a metal-bead-labeled binding agent.

12. The cartridge of claim 6, wherein said cartridge comprises at least one reagent-containing bead in at least one well in said base.

13. The cartridge of claim 6, wherein said cartridge comprises a nuclease in at least one of the wells in said base.

\* \* \* \* \*